United States Patent
Tomperi et al.

(10) Patent No.: US 7,741,362 B2
(45) Date of Patent: Jun. 22, 2010

(54) SOMATOSTATIN RECEPTOR 1 AND/OR 4 SELECTIVE AGONISTS AND ANTAGONISTS

(75) Inventors: Jussi Tomperi, Turku (FI); Paivi Hautamaki, Turku (FI); Harri Salo, Turku (FI); Mia Engstrom, Turku (FI); Andrei Tauber, Helsinki (FI); Anna-Marja Hoffren, Raisio (FI); Siegfried Wurster, Piikkio (FI)

(73) Assignee: Siegfried Wurster, Piikkio (FI)

( * ) Notice: Subject to any disclaimer, the term of this patent is extended or adjusted under 35 U.S.C. 154(b) by 1002 days.

(21) Appl. No.: 10/574,584

(22) PCT Filed: Oct. 5, 2004

(86) PCT No.: PCT/FI2004/000585

§ 371 (c)(1),
(2), (4) Date: Apr. 4, 2006

(87) PCT Pub. No.: WO2005/033069

PCT Pub. Date: Apr. 14, 2005

(65) Prior Publication Data

US 2007/0129422 A1 Jun. 7, 2007

Related U.S. Application Data

(60) Provisional application No. 60/508,268, filed on Oct. 6, 2003.

(30) Foreign Application Priority Data

Oct. 6, 2003 (FI) .................................. 20031454

(51) Int. Cl.
*A61K 31/40* (2006.01)
*A61K 31/38* (2006.01)
*A01N 41/06* (2006.01)
*A61K 31/18* (2006.01)
*C07D 209/36* (2006.01)
*C07D 333/00* (2006.01)

(52) U.S. Cl. ...................... 514/418; 514/443; 514/602; 548/484; 549/52

(58) Field of Classification Search .................. None
See application file for complete search history.

(56) References Cited

U.S. PATENT DOCUMENTS

| | | |
|---|---|---|
| 4,485,101 A | 11/1984 | Coy et al. |
| 5,409,894 A | 4/1995 | Handley |
| 6,124,256 A | 9/2000 | Hayry et al. |
| 6,221,870 B1 | 4/2001 | Pfaeffli et al. |
| 6,221,888 B1 | 4/2001 | Durette et al. |
| 6,271,252 B1 | 8/2001 | Chang et al. |
| 6,329,389 B1 | 12/2001 | Suzuki et al. |
| 6,352,982 B1 | 3/2002 | Mabuchi et al. |

FOREIGN PATENT DOCUMENTS

| | | |
|---|---|---|
| EP | 0 183 271 A2 | 6/1986 |
| WO | WO 97/03054 | 1/1997 |
| WO | WO 97/14715 | 4/1997 |
| WO | WO 97/43278 | 11/1997 |
| WO | WO 97/47317 | 12/1997 |
| WO | WO 98/53818 | 12/1998 |
| WO | WO 02/24192 A1 | 3/2002 |
| WO | WO 03/026575 A2 | 4/2003 |

OTHER PUBLICATIONS

Bonini, J.A. et al., "Identification and Characterization of Two G Protein-coupled Receptors for Neuropeptide FF," *Journal of Biological Chemistry* 275(50): 39324-39331 (Dec. 2000).
Reubi, J.C. et al., "A selective analog for the somatostatin sst1-receptor subtype expressed by human tumors," *European Journal of Phamacology* 345: 103-110 (1998).
Reubi, J.C. et al., "Somatostatin receptor sst1-sst5 expression in normal and neoplastic human tissues using receptor autoradiography with subtype-selective ligands," *European Journal of Nuclear Medicine* 28(7): 836-846 (Jul. 2001).
Rivier, J.E. et al., "Potent Somatostatin Undecapeptide Agonists Selective for Somatostatin Receptor 1 (sst1)," *Journal of Medicinal Chemistry* 44(13): 2238-2246 (2001).
Sinisi, A.A. et al., "Different Expression Patterns of Somatostatin Receptor Subtypes in Cultured Epithelial Cells from Human Normal Prostate and Prostate Cancer," *Journal of Clinical Endocrinology and Metabolism* 82(8): 2566-2569 (1997).
von Essen, R. et al., "Effects of Octreotide Treatment on Restenosis After Coronary Angioplasty: Results of the VERAS Study," *Circulation* 96(5): 1482-1487 (Sep. 1997).
Yang, H.-Y.T. et al., "Isolation, sequencing, synthesis, and pharmacological characterization of two brain neuropeptides that modulate the action of morphine," *Proc. National Academy of Science USA* 82: 7757-7761 (Nov. 1985).

(Continued)

*Primary Examiner*—Anish Gupta
*Assistant Examiner*—Marcel M Cordero Garcia
(74) *Attorney, Agent, or Firm*—Oliff & Berridge, PLC

(57) ABSTRACT

The invention relates to (hetero)arylsulfonylamino based peptidomimetics of formula (I), wherein R1, R2, R3, A, B, D, Q, k and n are defined as disclosed, or a pharmaceutically acceptable salt or ester thereof. Compounds of formula (I) possess high affinity and selectivity for the somatostatin receptor subtypes SSTR1 and/or SSTR4 and can be used for the treatment or diagnosis of diseases or conditions wherein an interaction with SSTR1 and/or SSTR4 is indicated to be useful.

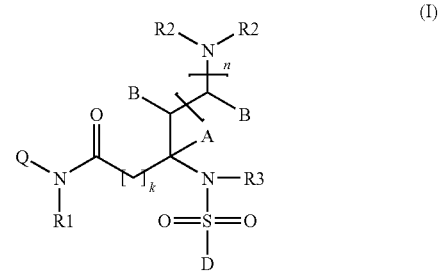

13 Claims, No Drawings

OTHER PUBLICATIONS

Hoyer, D. et al., "Classification and nomenclature of somatostatin receptors," *TiPS* 16: 86-88 (Mar. 1995).

Mazarguil, H. et al, "Structure-activity relationships of neuropeptide FF: role of C-terminal regions," *Peptides* 22: 1471-1478 (2001).

Mori, M. et al., "Differential expression of somatostatin receptors in the rat eye: SSTR4 is intensely expressed in the iris/ciliary body," *Neuroscience Letters* 223: 185-188 (1997).

Patel, Y.C., "Somatostatin and Its Receptor Family," *Frontiers in Neuroendocrinology* 20: 157-198 (1999).

Payza, K. et al., "Neuropeptide FF Receptors: Structure-Activity Relationship and Effect of Morphine," *Journal of Pharmacology and Experimental Therapeutics* 267(1): 88-94 (1993).

Reisine, T. et al., "Molecular Biology of Somatostatin Receptors," *Endocrine Reviews* 16(4): 427-442 (Aug. 1995).

Bourguignon, J.J. et al., "Analogs of NPFF, a neuropeptide which modulates morphine analgesia," *Proceedings of the XIVth International Symposium on Medicinal Chemistry*, pp. 35-44 (1997) (Elsevier Science B.V.).

Brussaard, A.B. et al., "Peripheral Injection of DNS-Injection RFa, A FMRFa Agonist, Suppresses Morphine-Induced Analgesia in Rats," *Peptides* 10: 735-739 (1989).

Cheng, Y.-C. et al., "Relationship between the Inhibition Constant ($K_1$) and the Concentration of Inhibitor which Causes 50 Per Cent Inhibition ($I_{50}$) of an Enzymatic Reaction," *Biochemical Pharmacology* 22: 3099-3108 (1973).

Curtis, S.B. et al., "Somatostatin receptor subtype expression and function in human vascular tissue," *Am. J. Physiol. Heart Circ. Physiol.* 278: H1815-H1822 (2000).

Eriksen, U.H. et al., "Randomized double-blind Scandinavian trial of angiopeptin versus placebo for the prevention of clinical events and restenosis after coronary balloon angioplasty," *American Heart Journal* 130(1): 1-8 (Jul. 1995).

Gicquel, S. et al., "Structure-Activity Study of Neuropeptide FF: Contribution of N-Terminal Regions to Affinity and Activity," *Journal of Medicinal Chemistry* 37(21): 3477-3481 (1994).

Rohrer, S.P. et al., "Rapid Identification of Subtype-Selective Agonists of the Somatostatin Receptor Through Combinatorial Chemistry," *Science* 282: 737-740 (Oct. 1998).

Aavik, E. et al., "Elimination of vascular fibrointimal hyperplasia by somatostatin receptor 1,4-selective agonist," *FASEB Journal* 16: 724-726 (May 2002).

Bito, H. et al., "Functional Coupling of SSTR4, a Major Hippocampal Somatostatin Receptor, to Adenylate Cyclase Inhibition, Arachidonate Release, and Activation of the Mitogen-activated Protein Kinase Cascade," *Journal of Biological Chemistry* 269(17): 12722-12730 (Apr. 1994).

SOMATOSTATIN RECEPTOR 1 AND/OR 4 SELECTIVE AGONISTS AND ANTAGONISTS

FIELD OF THE INVENTION

The present invention relates to (hetero)arylsulfonylamino based peptidomimetics, which are useful for treating or diagnosing medical disorders related to somatostatin receptor subtypes 1 and/or 4.

BACKGROUND OF THE INVENTION

Somatostatin is a cyclic peptide found endogenously in two major forms made up of 14 (sst-14) or 28 (sst-28) amino acids. The shorter sst-14 is identical in sequence to the C-terminal half of sst-28. Somatostatin is produced widely in the body and acts both systemically and locally to inhibit the secretion of various hormones, growth factors and neurotransmitters. The biological effects of somatostatin are mediated by a family of G protein-coupled receptors, of which five subtypes (SSTR1-5) have been cloned in humans (Reisine and Bell 1995; Patel 1999). The affinities of the two endogenous forms of somatostatin on the five subtypes are relatively similar (sst-28 has been reported to have a moderate preference for the SSTR5). However, the five subtypes are differentially expressed in different tissues and do also show some differences in their interaction with a number of signalling pathways. Thus, the pleiotropic physiological responses mediated by somatostatin are a reflection of its widespread distribution and the existence of multiple receptor subtypes.

Based on their sequence similarity and their affinity towards a number of octapeptide and hexapeptide analogs to somatostatin, the family of five somatostatin receptor subtypes can be divided into two subfamilies: one subfamily made up of SSTR2, SSTR3 and SSTR5 and another subfamily made up of SSTR1 and SSTR4. The former possesses high and the latter rather low affinity towards the aforementioned hexapeptide and octapeptide analogs (Hoyer et al. 1995). Due to the availability of high affinity and selective ligands, the physiology of the SSTR2,3,5 subfamily has been more thoroughly characterized and it appears that the 'classical' effects of somatostatin, such as very potent inhibition of growth hormone, insulin, glucagon and gastric acid release, are mediated either primarily or exclusively via members of this subfamily.

Even though the physiology and pathophysiology of the subtypes SSTR1 and SSTR4 are less well understood, there have been a number of findings about the role of these subtypes described in scientific publications and the patenting literature. U.S. Pat. No. 6,124,256 reported that, given their localisation in the vascular wall and their time-related induction during the proliferative stage, SSTR1 and/or SSTR4 may be the optimal subtypes to prevent fibroproliferative vasculopathy via a somatostatin receptor based therapy. In agreement with this, Curtis et al. (2000) have described SSTR1 and SSTR4 to represent the predominant subtypes expressed in human blood vessels and have proposed the use of SSTR1- or SSTR4-selective agonists for the treatment of endothelial cell-mediated proliferative diseases. Aavik et al. (2002) have demonstrated that a purportedly SSTR1- and SSTR4-selective peptide analogue of somatostatin (CH-275) is able to prevent intimal hyperplasia after rat carotid denudation injury. Taken together, these findings may explain why two peptide analogues of somatostatin, octreotide and lanreotide, which possess very high preferences for the subtypes SSTR2 and SSTR5 but have rather low affinities for the subtypes SSTR1 or SSTR4, failed to show efficacy in clinical trials aiming at the prevention of restenosis after percutaneous transluminal angioplasty (Eriksen et al. 1995; von Essen et al. 1997).

Due to the fact that SSTR1 activation causes antiproliferative effects, SSTR1-selective agonist may be useful for the treatment of SSTR1 bearing tumors. For example, it has been described that SSTR1 receptors are expressed in prostate cancer (Sinisi et al. 1997; Reubi et al. 1998; Reubi et al. 2001) but not in normal prostate tissue. Independent of its functional properties as an agonists or an antagonist, any SSTR1 selective ligand may be useful for the diagnosis of prostate tumors or tumors in other tissues expressing the SSTR1 subtype.

WO97/03054 and U.S. Pat. No. 6,221,870 describe benzo[g]quinoline-derived (WO097/03054) or ergoline-derived (U.S. Pat. No. 6,221,870) SSTR1-selective antagonist as lowering aggressive behavior in mice and, based on this observation, suggest such compounds to be useful for the treatment of depression, anxiety, affective disorders and attention deficit and hyperactivity disorders.

According to Bito et al. (1994) the SSTR4 subtype is expressed at high levels in the rat hippocampus where somatostatin has been reported to play a significant role in the regulation of membrane conductance. Since the hippocampus is a brain structure closely linked to learning and memory, as well as mental disorders such as depression and schizophrenia, the prominent role of the SSTR4 subtype in the hippocampus suggests that SSTR4 selective agonists or antagonists with the ability to pass the blood-brain-barrier may have therapeutic potential.

Employing in situ hybridisation, Mori et al. (1997) have shown that in the rat eye SSTR4 expression predominates in the posterior iris epithelium and ciliary body. In addition, the authors have observed that somatostatin lowers intraocular pressure (iop) and, based on these observations, they have suggested that SSTR4-selective ligands may be useful as anti-glaucoma agents.

Somatostatin has a very short biological half-life and is therefore unsuitable for therapeutic use. A number of shorter hexa- and octapeptide analogs of somatostatin with improved biological stability have been identified (e.g. patents U.S. Pat. No. 4,485,101, U.S. Pat. No. 5,409,894 or WO97/47317). However, these abbreviated peptide analogs are heavily biased in favour of the SSTR2,3,5 subfamily and do not show any significant interaction with the subtypes SSTR1 or SSTR4. In contrast, WO97/14715 and Rivier et al. (2001) describe a group of SSTR1 preferring undecapeptide agonists. However, besides their often rather short biological half-lifes peptides also possess other problematic properties, which make them unsatisfactory as medicines. For example, peptides have a very limited ability to penetrate membranes. This is one of the reasons, why it is in most cases impossible to apply peptides via an oral route and why peptides generally do not reach the central nervous system.

In recent years, a number of nonpeptide somatostatin agonists have been identified. Besides the already mentioned SSTR1-selective antagonists reported in WO97/03054 and U.S. Pat. No. 6,221,870, WO97/43278 describes a number of thiourea-based compounds that preferentially interact with the somatostatin SSTR4 and the histamin $H_3$ subtype. U.S. Pat. No. 6,329,389 and U.S. Pat. No. 6,352,982 provide SSTR4-selective compounds centred around tetrahydroquinoline or 4,1-benzoxazepine scaffolds. Rohrer et al. (1998) have been able to identify subtype-selective agonists for each of the five somatostatin receptor subtypes by employing a combinatorial chemistry strategy which incorporated the generally accepted hypothesis on the structure-activity-relationship of somatostatin receptor active compounds that the amino acid residues 8 and 9 in sst-14 (which consist of a tryptophan and a lysine) are essential for proper ligand-receptor interaction.

The current invention describes a new class of somatostatin receptor ligands in the form of sulfonamido-peptidomimetics. These compounds are in part related to sulfonamido-peptidomimetics, which have been presented in Brussaard et al. (1989), WO02/24192 and WO03/026575 in the context of another G-protein coupled receptor family, namely neuropeptide FF receptor. Sulfonamide derivatives of monocyclic or bicyclic amino acids have also been described in U.S. Pat. No. 6,271,252 and U.S. Pat. No. 6,221,888 as cell adhesion molecule (CAM) antagonists which inhibit leukocyte adhesion and leukocyte adhesion-mediated pathologies.

SUMMARY OF THE INVENTION

The present invention relates to non-peptide compounds possessing a high degree of selectivity towards the two receptor subtypes in the SSTR1/SSTR4 somatostatin receptor subfamily. It will be appreciated by those skilled in the art that, based on their agonism or antagonism at SSTR1 or SSTR4 receptor, a wide variety of therapeutic, prophylactic and diagnostic applications may be prepared from the compounds of this invention:

1. Compounds of the invention are useful for the prevention or treatment of diseases or symptoms of anxiety, depression, schizophrenia, epilepsy, attention deficit and hyperactive disorders and neurodegenerative diseases such as dementia, Alzheimer's disease and Parkinson's disease. The treatment of affective disorders includes bipolar disorders, e.g. manic-depressive psychoses, extreme psychotic states e.g. mania and excessive mood swings for which a behavioural stabilization is being sought. The treatment of anxiety states includes generalized anxiety as well as social anxiety, agoraphobia and those behavioural states characterized by social withdrawal, e.g. negative symptoms.

2. Compounds of the invention, depending on their agonistic or antagonistic character on the SSTR1 or SSTR4, are advantageous in diseases involving pathological vascular proliferation, e.g. angiogenesis, restenosis, smooth muscle proliferation, endothelial cell proliferation and new blood vessel sprouting or conditions requiring the activation of neovascularization. The angiogenic disease may for example be age-related macular degeneration or vascular proliferation associated with surgical procedures, e.g. angioplasty and AV shunts. Other possible uses are the treatments of arteriosclerosis, plaque neovascularization, hypertrophic cardiomyopathy, myocardial angiogenesis, valvular disease, myocardiac infarction, coronary collaterals, cerebral collaterals and ischemic limb angiogenesis.

3. Compounds of the invention are also indicated for the treatment of diseases connected to pathological condition in the retina and/or iris-ciliary body of mammals. Such conditions may be high intraocular pressure (IOP) and/or deep ocular infections. Treatable diseases may e.g. be glaucoma, stromal keratitis, iritis, retinitis, cataract and conjunctivitis. Other diseases connected to the eye may be ocular and corneal angiogenic conditions, for example, corneal graft rejection, retrolental fibroplasia, Osler-Webber Syndrome or rubeosis.

4. Compounds of the invention are also useful for the prevention or treatment of diseases or symptoms connected to diabetic complications such as diabetic retinopathy, diabetic nephropathy, diabetic neuropathy, Doan syndrome and orthostatic hypotension.

5. Compounds of the invention are useful for the treatment of a number of tumors such as e.g. the proliferation of adenoma cells, thyroid cancer, large bowel cancer, breast cancer, prostatic cancer, small cell lung cancer, non-small cell cancer, pancreatic cancer, stomach cancer, GI tumors, cholangiocarcinoma, hepatic cancer, vesical cancer, ovarian cancer, melanoma, osteosarcoma, chondrosarcoma, malignant pheochromocytoma, neuroblastoma, brain tumors, thymoma, paragangliomas, prostate carcinomas, sarcomas, gastroenteropancreatic tumors, gastric carcinomas, phaeochromocytomas, ependymomas, renal cancers, leukemia e.g., leukemia of basophilic leukemia, chronic lymphocytic leukemia, chronic myeloid leukemia, Hodgkin disease and non-Hodgkin lymphoma.

6. Compounds of the invention can also be used for the imaging of healthy or diseased tissues and/or organs, such as brain, vessels or tumors, possessing SSTR1 and/or SSTR4 receptors.

7. Compounds of the invention are useful for targeting tumors with SSTR1 and/or SSTR4 receptors using a compound of the invention conjugated with anti-cancer drugs directly or using a suitable spacer.

8. Finally, compounds of the invention are useful for wound healing, ovulation, menstruation, placentation, peptic ulcers, psoriasis, rheumatoid arthritis and Crohn's disease.

DETAILED DESCRIPTION OF THE INVENTION

The invention relates to the use of compounds having general formula (I) and pharmaceutically acceptable salts and esters thereof for the preparation of a medicament for treating a disease or condition in mammals where an interaction with the somatostatin receptor subtypes 1 and/or 4 is indicated to be useful,

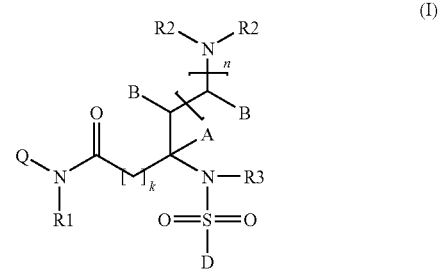

(I)

wherein

Q is

1) H, 2) aryl, 3) heteroaryl or 4) a group of formula

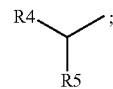

;

wherein aryl and heteroaryl can be unsubstituted or substituted with 1 to 4 substituents selected from $R^a$;

A is
1) H,
2) $(C_1-C_6)$alkyl or
3) $(C_3-C_5)$cycloalkyl;

B is independently selected from
1) H,
2) halogen or
3) $(C_1-C_6)$alkyl;
or B and B together can form a double or a triple bond between the atoms to which they are attached;

D is aryl or heteroaryl, which can be unsubstituted or substituted with one to four groups selected from $R^d$;

R1 is
1) H,
2) $(C_1-C_6)$alkyl or
3) $(C_3-C_7)$cycloalkyl;

R2 is independently selected from
1) H,
2) $(C_1-C_6)$alkyl,
3) $(C_2-C_6)$alkenyl,
4) $(C_2-C_6)$alkynyl,
5) $(C_3-C_7)$cycloalkyl,
6) $(C_3-C_7)$cycloalkyl$(C_1-C_6)$alkyl,
7) —$NH_2$ or
8) —$C(=NR^b)NR^bR^b$;
wherein $R^b$ and $R^b$ together with the atoms to which they are attached can also form a 5 to 6 membered unsaturated or saturated ring; or
R2 and R2 together with the nitrogen to which they are attached form a 5 to 7 membered ring containing 1 to 3 heteroatoms selected from N, O and S, wherein the formed ring can be saturated or unsaturated;

R3 is
1) H,
2) $(C_1-C_6)$alkyl,
3) $(C_2-C_6)$alkenyl,
4) $(C_2-C_6)$alkynyl or
5) $(C_3-C_7)$cycloalkyl;

R4 is
1) H,
2) $(C_1-C_6)$alkyl,
3) $(C_2-C_6)$alkenyl,
4) $(C_2-C_6)$alkynyl,
5) Cy,
6) Cy-$(C_1-C_6)$alkyl,
7) Cy-$(C_2-C_6)$alkenyl or
8) Cy-$(C_2-C_6)$alkynyl;
wherein alkyl, alkenyl, alkynyl and Cy are each optionally substituted with one to two substituents selected from $R^d$;

R5 is
1) H,
2) $(C_1-C_6)$alkyl,
3) $(C_2-C_6)$alkenyl,
4) $(C_2-C_6)$alkynyl,
5) aryl,
6) aryl-$(C_1-C_6)$alkyl,
7) heteroaryl,
8) heteroaryl$(C_1-C_6)$alkyl or
9) —$(CH_2)_kC(O)NHR^b$;
wherein aryl and heteroaryl are each optionally substituted with one to two substituents selected from $R^d$; or R4 and R5 together with the atom to which they are attached form a 3 to 7 membered ring containing 0 to 2 heteroatoms selected from N, O and S, wherein the said ring can be substituted with one to three substituents selected from $R^d$; or the said ring can be fused to aryl or heteroaryl which can be substituted with one to three substituents selected from $R^d$;

$R^a$ is independently
1) H,
2) halogen,
3) —$OR^b$,
4) $(C_1-C_6)$alkyl or
5) —$CF_3$;

$R^b$ is independently
1) hydrogen,
2) $(C_1-C_6)$alkyl,
3) $(C_2-C_6)$alkenyl,
4) $(C_2-C_6)$alkynyl,
5) Cy or
6) Cy-$(C_1-C_4)$alkyl;

$R^d$ is independently
1) a group selected from $R^c$,
2) $(C_1-C_6)$alkyl,
3) $(C_2-C_6)$alkenyl,
4) $(C_2-C_6)$alkynyl,
5) aryl,
6) aryl-$(C_1-C_6)$alkyl,
7) heteroaryl-$(C_1-C_6)$alkyl,
8) $(C_3-C_7)$cycloalkyl or
9) heterocyclyl;
wherein alkyl, alkenyl, alkynyl, aryl and heteroaryl are each optionally substituted with one to four substituents independently selected from $R^c$;

$R^c$ is independently
1) a group selected from $R^a$,
2) —$NO_2$,
3) —$SR^b$,
4) —$NR^bR^b$,
5) —CN or
6) —$NR^bC(O)R^b$;

k is an integer 0 or 1;
n is an integer from 0 to 3; and
Cy is cycloalkyl, heterocyclyl, aryl or heteroaryl.

"Alkyl", as well as other groups having the prefix "alk", such as alkoxy, alkanoyl, means carbon chains which may be linear or branched or combinations thereof. Size of the alkyl can further be specified by adding the number of carbons in front of the group, e.g. $(C_1-C_6)$alkyl, $(C_1-C_3)$alkyl. Examples of alkyl groups include methyl, ethyl, propyl, isopropyl, butyl, sec-butyl, tert-butyl, pentyl, neopentyl, hexyl, heptyl, octyl, nonyl, and the like.

"Alkenyl" means carbon chains which contain at least one carbon-carbon double bond, and which may be linear or branched or combinations thereof. Size of the alkenyl can further be specified by adding the number of carbons in front of the group, e.g. $(C_2-C_6)$alkenyl, $(C_2-C_8)$alkenyl. Examples of alkenyl groups include vinyl, allyl, isopropenyl, 1-pentenyl, 2-pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Size of the alkynyl can further be specified by adding the number of carbons in front of the group, e.g. $(C_2-C_6)$alkynyl, $(C_2-C_8)$alkynyl. Examples of alkynyl groups include ethynyl, propargyl, 3-methyl-1-pentynyl, 2-heptenyl, and the like.

"Cycloalkyl" means mono- or bicyclic saturated carbocyclic rings, each of which having from 3 to 8 carbon atoms. The term also includes monocyclic rings fused to an aryl group in which the point of attachment is on the non-aromatic portion.

Size of the cycloalkyl can further be specified by adding the number of carbons in front of the group, e.g. $(C_3-C_7)$cycloalkyl, $(C_5-C_{10})$-cycloalkyl. Examples of cycloalkyl groups include cyclopropyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also include aryl group fused to a monocyclic cycloalkyl or monocyclic heterocyclyl group in which the point of attachment is on the aromatic portion. Size of the aryl can further be specified by adding the number of carbons in front of the group, e.g. $(C_6-C_{12})$aryl. Examples of aryl groups include phenyl, naphthyl, indanyl, indenyl, tetrahydronaphthyl, 2,3-dihydrobenzofuranyl, benzopyranyl, 1,4-benzodioxanyl, and the like.

"Heteroaryl" means a mono- or bicyclic aromatic ring containing at least one heteroatom selected from N, O and S, with each ring containing 5 to 6 atoms. The term also include heteroaryl group fused to a monocyclic cycloalkyl or monocyclic heterocyclyl group in which the point of attachment is on the aromatic portion. Examples of heteroaryl groups include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3b)pyridyl, quinolyl, indolyl, isoquinolyl, and the like.

"Heterocyclyl" means mono- or bicyclic saturated rings containing at least one heteroatom selected from N, O, S, each of said ring having from 5 to 8 atoms in which the point of attachment may be carbon or nitrogen. The term also includes monocyclic heterocycle fused to an aryl or a heteroaryl group in which the point of attachment is on the non-aromatic portion. Furthermore, the term also includes partially unsaturated monocyclic rings that are not aromatic, such as 2- and 4-pyridones attached through the nitrogen. Other examples of heterocyclyl groups include pyrrolidinyl, piperidinyl, piperazinyl, imidazolinyl, 2,3-dihydrofuro(2,3-b)pyridyl, benzoxazinyl, tetrahydroquinolinyl, tetrahydroisoquinolinyl, dihydroindonyl, and the like.

The term "cycloalkyl-alkyl", as employed herein, refers to a "cycloalkyl", as defined above, appended to the parent molecular moiety through an alkyl group, as defined above. Size of the cycloalkyl and the alkyl can further be specified by adding the number of carbons in front of the group, e.g. $(C_3-C_7)$cycloalkyl$(C_1-C_6)$alkyl, $(C_3-C_5)$cycloalkyl$(C_1-C_2)$alkyl. Representative examples of cycloalkyl-alkyl include, but are not limited to, cyclohexylmethyl, 1-cyclohexylethyl, 2-cyclopentylethyl, and the like.

The term "aryl-alkyl", as employed herein, refers to a "aryl", as defined above, appended to the parent molecular moiety through an $(C_1-C_6)$alkyl group, as defined above. Size of the aryl or alkyl can further be specified by adding the number of carbons in front of the group, e.g. aryl-$(C_1-C_6)$alkyl, $(C_6-C_{12})$aryl-$(C_1-C_3)$alkyl. Representative examples of aryl-alkyl include, but are not limited to, 2-naphthylmethyl, 1-(2-indanyl)ethyl, 2-tetrahydronaphthylethyl, and the like.

The term "heteroaryl-alkyl", as employed herein, refers to a "heteroaryl", as defined above, appended to the parent molecular moiety through an alkyl group, as defined above. Size of the alkyl can further be specified by adding the number of carbons in front of the group, e.g. heteroaryl-$(C_1-C_6)$alkyl, heteroaryl-$(C_1-C_2)$alkyl. Representative examples of heteroaryl-alkyl include, but are not limited to, 2-(2-pyridyl) propyl, 2-benzothiophenylmethyl, 4-(2-quinolyl)butyl, and the like.

The term "Cy-alkyl", as employed herein, refers to a "Cy", as defined above, appended to the parent molecular moiety through an alkyl group, as defined above. Size of the alkyl can further be specified by adding the number of carbons in front of the group, e.g. Cy-$(C_1-C_6)$alkyl, Cy-$(C_1-C_3)$alkyl. Representative examples of Cy-alkyl include, but are not limited to, benzyl, 1-(2-naphthyl)ethyl, 2-cyclohexylethyl, and the like.

The term "halogen", as employed herein, refers to chlorine, bromine, fluorine or iodine.

The compounds of formula I, as well as the pharmaceutically acceptable salts and esters thereof, are referred to below as the compounds of the invention, unless otherwise indicated.

The invention includes within its scope all the possible stereoisomers of the compounds, including geometric isomers, e.g. Z and E isomers (cis and trans isomers), and optical isomers, e.g. diastereomers and enantiomers. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of optical isomers, e.g. enantiomers, from the mixture thereof the conventional resolution methods, e.g. fractional crystallisation, may be used.

Some of the compounds of the invention may also exist as tautomers, namely having different points of attachment of hydrogen. For instance, ketones can exist also in their enol form (keto-enol tautomerism). The individual tautomers as well as mixtures thereof are encompassed with compounds of invention.

Pharmaceutically acceptable salts, e.g. acid addition salts with both organic and inorganic acids are well known in the field of pharmaceuticals. Non-limiting examples of these salts include chlorides, bromides, sulfates, nitrates, phosphates, sulfonates, formates, tartrates, maleates, citrates, benzoates, salicylates and ascorbates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl and tert-butyl esters.

The pharmaceutical compositions of the compounds of the invention may be formulated in a conventional manner using one or more pharmaceutically acceptable carriers or excipients. Formulations can for instance enable for oral, buccal, topical, intranasal, parenteral (e.g. intravenous, intramuscular or subcutaneous) or rectal administration or administration by inhalation or insufflation. Compounds of the invention may also be formulated for sustained delivery.

For oral administration, forms of suitable compositions include but are not limited to tablets, chewable tablets and capsules. These may be prepared by conventional means with pharmaceutically acceptable excipients, such as binding agents (e.g. pregelatinized maize starch), disintegrants (e.g. potato starch), fillers (e.g. lactose) or lubricants (e.g. magnesium stearate). Tablets may be coated by methods well known in the art. For oral administration, possible liquid preparations include but are not limited to solutions, syrups or suspensions, or they may exist as dry powder for constitution with water or other suitable vehicle prior use. These liquid preparations may be prepared by conventional means with pharmaceutically acceptable agents, such as suspending agents, non-aqueous vehicles, preservatives and emulsifyiers.

A possible dose of the active compounds of the invention for oral, parenteral, buccal or topical dose to the adult human is between 0.1 and 500 mg of the active compound per unit dose, which may administered, for instance, 1 to 4 times in a day.

It is well recognized that the precise dose, the route of administration and the dosing interval can be determined by those skilled in the art. It is also well recognized that these variables depend on multiple factors including but not restricted to activity of the therapeutic compound, the formulation thereof, pharmacokinetic properties (such as absorption, distribution, metabolism and excretion) of the therapeutic compound, the nature and location of the target tissue or organ and the issues connected to the state of a disease or disorder in a patient in need of treatment. Additionally, when the compounds of the invention are administered with additional pharmaceutically active ingredients, one or more pharmaceutical compositions may be used for the delivery of all the agents, which may be administered together, or at different times, as determined by those skilled in the art.

The compounds of the current invention can be viewed as consisting of three different motifs: an 'aromatic part', a 'carboxylic acid' and a 'sulfonylamino' part. Thus, the compounds of the invention are named as amides wherein the 'carboxylic acid' forms the parent structure that is amidated by the 'aromatic part' and further substituted by the 'sulfonylamino' and an additional basic function. Naming is exemplified with the following structures:

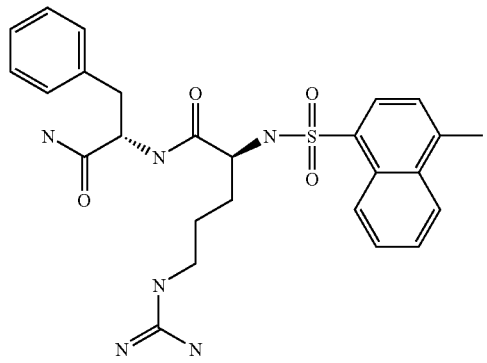

N-((S)-1-carbamoyl-2-phenylethyl)-5-guanidino-(S)-2-(N'-(4-methyl-1-naphthalenesulfonyl)amino)pentanamide

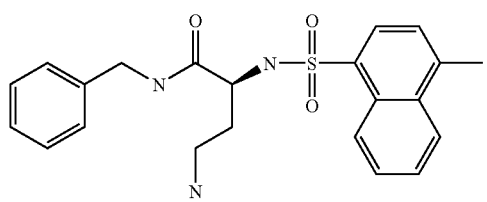

N-benzyl-4-(N'-isopropyl)amino-(S)-2-(N''-(4-methyl-1-naphthalenesulfonyl)amino)butanamide One preferred embodiment of the compounds of formula I are those wherein Q is

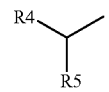

and R5 is —C(O)NH$_2$. For this purpose R4 is preferably Cy or Cy-(C$_1$-C$_3$)alkyl where Cy is optionally substituted with one to three substituents selected from R$^d$; even more preferred Cy is phenyl. Preferred substitutents are selected from halogen, (C$_1$-C$_3$)alkyl and —O(C$_1$-C$_3$)alkyl.

Another preferred embodiment of the compounds of formula I are those wherein Q is

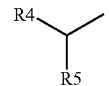

and R5 is —C(O)NH$_2$. For this embodiment R4 is preferably benzyl where the benzylic carbon is substituted with an additional phenyl.

Another preferred embodiment of the compounds of formula I are those wherein Q is

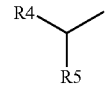

and R5 is hydrogen or (C$_1$-C$_3$)alkyl and R4 is phenyl or benzyl, optionally substituted at positions 2 or 3 with one to two substituents selected from R$^d$. More preferred substituents are selected from halogen and (C$_1$-C$_3$)alkyl.

Another preferred embodiment of the compounds of formula I are those where R1 is hydrogen or (C$_1$-C$_3$)alkyl and more preferably hydrogen.

Yet another preferred embodiment of the compounds of formula I are those where R2 is hydrogen, (C$_1$-C$_3$)alkyl, (C$_3$-C$_5$)cycloalkyl or —C(=NH)NH$_2$.

Yet another preferred embodiment of the compounds of formula I are those where R3 is hydrogen or (C$_1$-C$_6$)alkyl.

Yet another preferred embodiment of the compounds of formula I are those where A is hydrogen.

Yet another preferred embodiment of the compounds of formula I are those where B is hydrogen.

Yet another preferred embodiment of the compounds of formula I are those where D is aryl, which is optionally substituted with one to three substituents selected from R$^d$. In a more preferred embodiment D is naphthyl, which is optionally substituted with one to two groups selected from R$^d$ and preferred substitutions are selected from halogen, (C$_1$-C$_6$) alkyl, —NR$^b$R$^b$ and —OR$^b$. Even more preferred substitutions are halogen and (C$_1$-C$_3$)alkyl.

Yet another preferred embodiment of the compounds of formula I are those where n is an integer 1 or 2.

Yet another preferred embodiment of the compounds of formula I are those where k is 0.

Yet another preferred embodiment of the compounds of formula I are those where the absolute configuration of the carbon containing the group A substitution is S.

In another aspect the invention provides novel compounds of formula II,

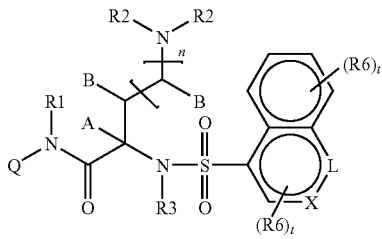

and pharmaceutically acceptable salts and esters thereof, wherein R1, R3, A, B and Q are as defined above under formula I, and R2 is independently selected from
1) H,
2) $(C_1-C_6)$alkyl,
3) $(C_2-C_6)$alkenyl,
4) $(C_2-C_6)$alkynyl,
5) $(C_3-C_7)$cycloalkyl or
6) $(C_3-C_7)$cycloalkyl$(C_1-C_6)$alkyl;
or symbols R2 together with the nitrogen to which they are attached form a saturated 5 to 7 membered ring containing 1 to 2 heteroatoms selected from N, O and S;

and when Q is a group of formula

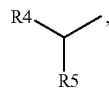

then R4 is as defined above under formula I;
R5 is
1) H,
2) $(C_1-C_6)$alkyl,
3) $(C_2-C_6)$alkenyl,
4) $(C_2-C_6)$alkynyl,
5) aryl,
6) aryl-$(C_1-C_6)$alkyl,
7) heteroaryl or
8) heteroaryl-$(C_1-C_6)$alkyl;
wherein aryl and heteroaryl are each optionally substituted with one to four substituents selected from $R^d$; or
R4 and R5 together with the atom to which they are attached form a 3 to 8 membered ring containing 0 to 2 heteroatoms selected from N, O and S, wherein the said ring may be substituted with one to three substituents selected from $R^d$; or the said ring may be fused to aryl or heteroaryl which may be substituted with one to three substituents selected from $R^d$;
R6 is independently selected from
1) H,
2) halogen,
3) —$NO_2$,
4) —$NR^bR^b$,
5) —CN,
6) —$OR^b$,
7) —$SR^b$,
8) —$C(O)R^b$,
9) $(C_1-C_6)$alkyl,
10) $(C_2-C_6)$alkenyl,
11) $(C_2-C_6)$alkynyl,
12) $(C_3-C_7)$cycloalkyl or
13) —$CF_3$;
t is an integer from 0 to 3;
n is an integer from 1 to 2;
X is a bond or C(R6);
L is C(R6), S or N; and
$R^b$ and $R^d$ are as defined above under formula I.

In a more preferred embodiment of Formula II, Q is

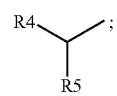

R1 is H; R2 is independently H or $(C_1-C_6)$alkyl; R3 is H or $(C_1-C_3)$alkyl; R4 is phenyl or benzyl optionally substituted by a group selected from $R^a$ as defined above under formula I; R6 is independently selected from H, halogen, $(C_1-C_6)$alkyl or —$CF_3$; t is an integer 0 to 1; A is H; B is H; L is C(R6), X is C(R6); and R5 and n are as defined above under formula II.

Yet another preferred embodiment of the compounds of formula II are those where the carbon containing the group A has the absolute configuration S.

EXPERIMENTAL PART

List of Abbreviations:
ACN acetonitrile
Boc tert-butyloxycarbonyl
BSA bovine serum albumin
2-Cl—Z 2-chloro-benzyloxycarbonyl
DBU 1,8-diazabicyclo[5.4.0]undec-7-ene
DCM dichloromethane
DIC diisopropylcarbodiimide
DIPEA N,N-diisopropylethylamine
DMF N,N-dimethylformamide
EDTA ethylenediamine-tetraacetic acid
ESI electrospray ionization
Fmoc 9-fluorenylmethoxycarbonyl
HEPES N-(2-hydroxyethyl)piperazine-N'-2-ethane-sulfonic acid
HOBt 1-hydroxybenzotriazole
HPLC high performance liquid chromatography
LC liquid chromatography
MS mass spectrometry
Pbf 2,2,4,6,7-pentamethyldihydrobenzofuran-5-sulfonyl
PG protecting group
Pmc 2,2,5,7,8-pentamethylchroman-6-sulfonyl
RP-HPLC reversed-phase high performance liquid chromatography
TEA triethylamine
TFA trifluoroacetic acid
THF tetrahydrofuran
TLC thin layer chromatography
TMOF trimethyl orthoformate
TMS tetramethylsilane
TRIS tris(hydroxymethyl)aminomethane Compounds of the invention can be prepared using the following general synthetic schemes.

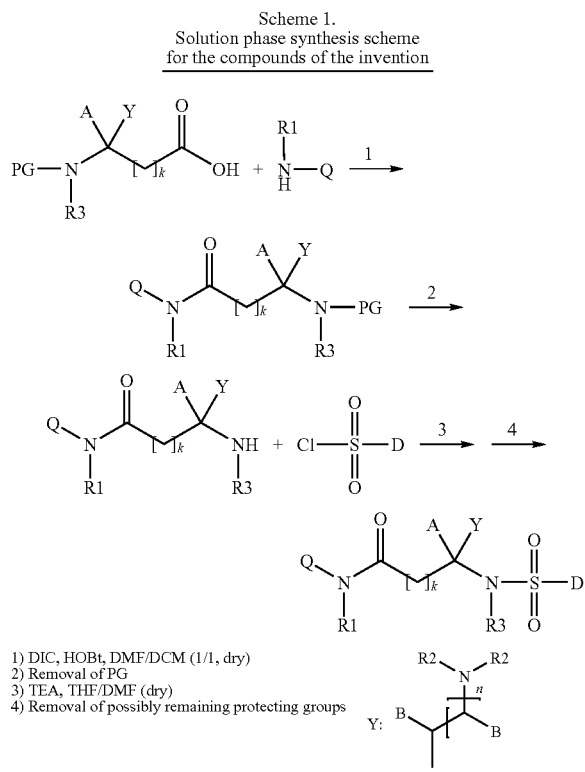

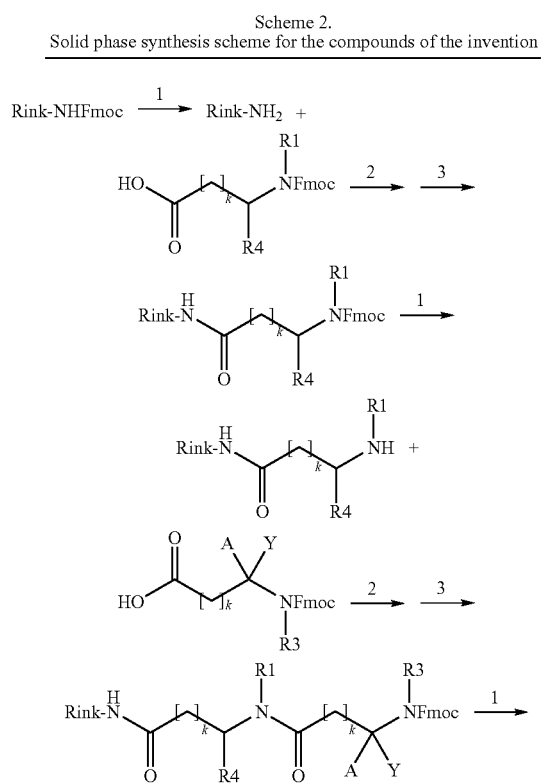

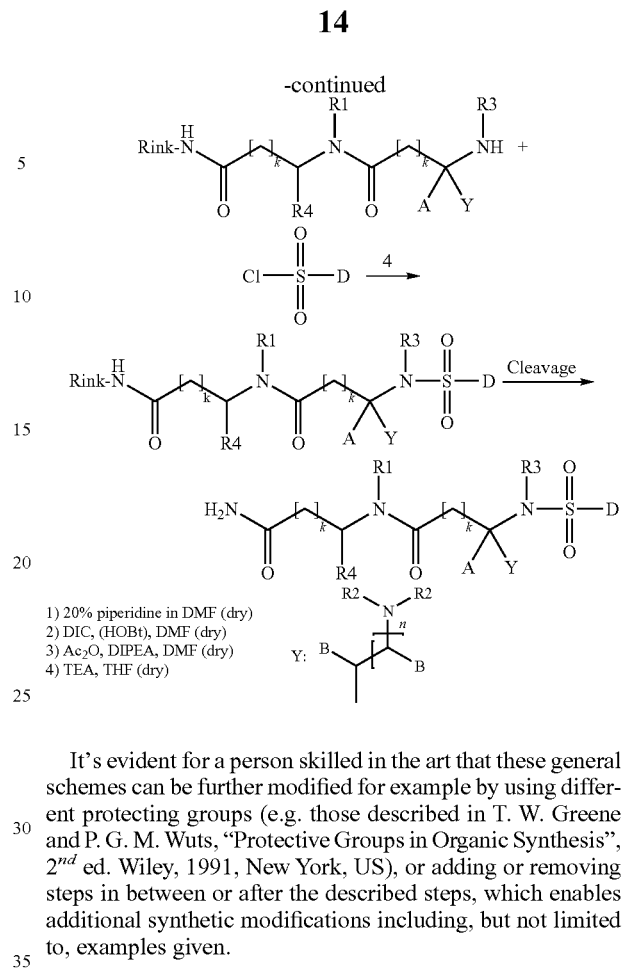

It's evident for a person skilled in the art that these general schemes can be further modified for example by using different protecting groups (e.g. those described in T. W. Greene and P. G. M. Wuts, "Protective Groups in Organic Synthesis", $2^{nd}$ ed. Wiley, 1991, New York, US), or adding or removing steps in between or after the described steps, which enables additional synthetic modifications including, but not limited to, examples given.

Starting Materials

The Rink resin was obtained from Advanced ChemTech, UK. Amino acids were purchased from either from Advanced ChemTech, UK or Novabiochem, Switzerland unless otherwise specified. DIC, HOBt, acetic anhydride and piperidine were products of Acros Organics, Belgium. DIPEA was from Fluka AG, Germany. All the other reagents or solvents were purchased from Aldrich or Merck, Germany, if not otherwise specified. The reagents were used as such and solvents were purified and dried according the methods described in W. L. F. Armareggo and D. D. Perrin, "Purification of Laboratory Chemicals", $4^{th}$ ed. Butterworth-Heinemann, 1996, Bath, Great Britain.

General Description of MS Analysis

Molecular weight of the compound was determined with Micromass Micro triple quadrupole mass spectrometer. Essential MS parameters were: cone voltage 30 V, capillary voltage 3.5 kV, low mass resolution on MS1 15, high mass resolution on MS1 15, ion energy on MS1 1.0, source temperature 110° C., desolvation temperature 250° C. and desolvation gas flow 700 l/h. Samples were introduced by Waters Alliance 2695 HPLC. Flow rate of 0.3 ml/min was formed of 10% water and 90% MeOH eluent (containing 0.01% HCOOH). Sample volume of 10 µl was injected through a Waters Symmetry Shield 2.1×10 mm $C_{18}$ precolumn.

General Description of LC-MS Analysis

For LC-MS analysis the gradient started from 100% water (containing 0.01% HCOOH) (A) which changed linearly in ten minutes to 100% ACN (containing 0.01% HCOOH) (B). In addition, a Waters Symmetry Shield 2.1×50 mm $C_{18}$ column with a corresponding precolumn was flushed for two minutes with B. Flow rate was 0.4 ml/min and 10 µl of sample was injected. Some essential MS parameters were increased compared to standard MS analysis: desolvation temperature to 350° C. and desolvation gas flow to 900 l/h. UV chromatogram was recorded with Waters 996 diode array detector.

General Description of NMR Analysis

NMR spectra were recorded on Bruker DMX 500 spectrometer operating at 500.13 MHz for $^1$H. $CD_3OD$ was used as the solvent and TMS as internal standard.

General Description of Flash Chromatography Purification

Flash Chromatographic purification were conducted with Argonaut FlashMaster II Automated Purification System (Argonaut Technologies, UK) using normal phase columns (Supelco DSC-Si 20 g). Flow rate was 7 ml/min and detection wavelength 230 nm. Standard elution program was 25 minutes with the following gradient: 100% DCM for 3 minutes followed by gradual increase up to 25% MeOH during 17 minutes and a gradual increase up to 100% of MeOH during the final 5 minutes. After MS verification, fractions containing the product were combined and evaporated.

General Description of RP-HPLC Purification

Semi-preparative RP-HPLC purifications were done with Waters 616 pump, controlled by Waters 600 controller unit. Instrument was equipped with Waters 2487 UV detector and Waters fraction collector. Xterra Prep $C_{18}$ RP 10×150 mm column with 7.8×20 mm precolumn was used for purifications. Flow rate was 6.6 ml/min and the detection wavelength 254 nm. Gradient started with water (containing 0.3% HCOOH) (A) which changed linearly to ACN (containing 0.3% HCOOH) (B) within ten minutes. In addition column was flushed with B for two minutes. Fraction collector was programmed to collect 30 s fractions. The fractions were analysed by MS.

General Description of LC Purity Analysis

HPLC purity of the compounds was determined using Waters 616 pump, controlled by Waters 600 controller unit. Instrument was further equipped with Waters 2487 UV detector (detection wavelengths 254 nm and 220 nm). Waters Symmetry Shield 2.1×50 mm $C_{18}$ column with corresponding precolumn and a flow rate of 0.4 ml/min was used. Linear gradient starting from water (containing 0.01% HCOOH) (A) to acetonitrile (containing 0.01% HCOOH) (B) over 17 minutes and then 100% B for 1 minute was applied.

Example 1

Synthesis of 5-amino-N-(3-chlorobenzyl)-(S)-2-(N'-(1-naphthalenesulfonyl)amino)pentanamide Step I Fmoc-Orn(Boc)-OH (70.0 mg, 454.52 g/mol, 0.15 mmol, 1 eq), DIC (24.1 µl, 126.20 g/mol, 0.806 g/cm$^3$, 0.15 mmol, 1 eq) and HOBt (20.8 mg, 135.12 g/mol, 0.15 mmol, 1 eq) were dissolved in dry DMF/DCM (1/1, 5 ml). After 5 minutes 3-chlorobenzylamine (18.8 µl, 141.60 g/mol, 1.159 g/cm$^3$, 0.15 mmol, 1 eq, Acros) was added to the reaction mixture. According to TLC analysis, reaction was complete after overnight stirring. Solvent was then evaporated and the yellow residue was purified with flash chromatography. 5-(N-Boc-amino)-N'-(3-chlorobenzyl)-(S)-2-(N''-Fmoc-amino)pentanamide as white foam was obtained with quantitative yield.

Step II

Fmoc protection was removed by dissolving the 5-(N-Boc-amino)-N'-(3-chlorobenzyl)-(S)-2-(N''-Fmoc-amino)pentanamide in 5 ml of 20 vol-% piperidine in DMF. After 30 minutes stirring, solvent and excess of piperidine were evaporated. Product was used without purification for step III.

Step III (S)-2-Amino-5-(N-Boc-amino)-N'-(3-chlorobenzyl)pentanamide (0.15 mmol) was dissolved in DMF (2.5 ml, dry) and 1-naphthalenesulfonyl chloride (45.4 mg, 226.68 g/mol, 0.2 mmol, 1.3 eq, Acros) in THF (2.5 ml, dry) was added. TEA (27.8 µl, 101.19 g/mol, 0.73 g/cm$^3$, 0.2 mmol, 1.3 eq, Baker) was then added to the solution. After 15 minutes, some precipitate was observed. After overnight stirring, solvent was evaporated and residue purified with flash chromatography to give 5-(N-Boc-amino)-N'-(3-chlorobenzyl)-(S)-2-(N''-(1-naphthalenesulfonyl)amino)pentanamide.

Step IV 5-(N-Boc-amino)-N'-(3-chlorobenzyl)-(S)-2-(N''-(1-naphthalenesulfonyl)amino)pentanamide was dissolved in 25% TFA in DCM (2 ml) and mixture was stirred for 30 minutes. Solvent evaporation gave 75.8 mg of 5-amino-N-(3-chlorobenzyl)-(S)-2-(N'-(1-naphthalenesulfonyl)amino) pentanamide as brown oil. Part of the product was further purified with RP-HPLC to give 11.5 mg of 5-amino-N-(3-chlorobenzyl)-(S)-2-(N'-(1-naphthalenesulfonyl)amino) pentanamide as a white powder, overall yield 13%.

MS-ESI$^+$ (m/z): 446

$^1$H NMR (500 MHz, $CD_3OD$; δ, ppm): 8.70 (m, 1H), 8.21 (m, 1H), 8.13 (d, 1H), 8.01 (m, 1H), 7.66-7.60 (m, 2H), 7.53 (m, 1H), 7.24-7.17 (m, 2H), 7.02 (m, 1H), 6.84 (m, 1H), 3.87 (d, 2H), 3.80 (m, 1H), 2.82 (m, 2H), 1.76-1.57 (m, 4H).

Example 2

Synthesis of 5-amino-(S)-2-(N-(4-methyl-1-naphthalenesulfonyl)amino)-N'-(phenyl)pentanamide Step I Fmoc-Orn(Boc)-OH (50.0 mg, 454.52 g/mol, 0.11 mmol, 1 eq), DIC (17.2 µl, 126.20 g/mol, 0.806 g/cm$^3$, 0.11 mmol, 1 eq) and HOBt (15.0 mg, 135.12 g/mol, 0.12 mmol, 1 eq) were dissolved in dry DMF/DCM (1/1, 4 ml). After 10 minutes aniline (10.0 µl, 93.13 g/mol, 1.022 g/cm$^3$, 0.11 mmol, 1 eq, Acros) was added to the reaction mixture. After overnight stirring, temperature was raised to 40° C. and kept there for 2 hours. Solvent was then evaporated and residue purified with flash chromatography. 5-(N-Boc-amino)-(S)-2-(N'-Fmoc-amino)-N''-(phenyl)pentanamide as white powder was obtained with quantitative yield.

Step II

Fmoc protection was removed by dissolving the 5-(N-Boc-amino)(S)-2-(N'-Fmoc-amino)-N''-(phenyl)pentanamide in 5 ml of 20 vol-% piperidine in DMF. After 45 minutes stirring, solvent and excess of piperidine were evaporated. Product was used without purification for step III.

Step III (S)-2-Amino-5-(N-Boc-amino)-N'-(phenyl)pentanamide (0.11 mmol) was dissolved in DMF (1 ml, dry) and 4-methyl-1-naphthalenesulfonyl chloride (26.5 mg, 240.71 g/mol, 0.11 mmol, 1 eq, Maybridge) in THF (1 ml, dry) was added. Finally, TEA (15.3 µl, 101.19 g/mol, 0.73 g/cm$^3$, 0.11 mmol, 1 eq, Baker) was added to the solution. After 15 minutes, some precipitate was observed. After overnight stirring, solvent was evaporated and residue purified with flash chromatography to give 5-(N-Boc-amino)-(S)-2-(N'-(4-methyl-1-naphthalenesulfonyl)amino)-N''-(phenyl)pentanamide.

Step IV 5-(N-Boc-amino)-(S)-2-(N'-(4-methyl-1-naphthalenesulfonyl)amino)-N''-(phenyl)pentanamide was dissolved in 30% TFA in DCM (3 ml) and mixture was stirred for 45 minutes. After solvent evaporation and flash chromatography 21.8 mg of 5-amino-(S)-2-(N-(4-methyl-1-naphthalenesulfonyl)amino)-N'-(phenyl)pentanamide was obtained; yield 48%.

MS-ESI$^+$ (m/z): 412

$^1$H NMR (500 MHz, CD$_3$OD; δ, ppm): 8.73 (m, 1H), 8.15 (d, 1H), 7.99 (m, 1H), 7.75-7.60 (m, 2H), 7.32 (m, 1H), 7.15-7.09 (m, 2H), 7.00 (m, 1H), 6.80 (m, 2H), 3.79 (m, 1H), 2.92 (m, 2H), 2.50 (d, 3H), 1.90-1.60 (m, 4H).

Example 3

Synthesis of 5-amino(S)-2-(N-(4-methyl-1-naphthalenesulfonyl)amino)-N'-((R)-1-(2-naphthyl)ethyl)pentanamide Step I Fmoc-Orn(Boc)-OH (100.2 mg, 454.52 g/mol, 0.22 mmol, 1 eq), DIC (34.4 µl, 126.20 g/mol, 0.806 g/cm$^3$, 0.22 mmol, 1 eq) and HOBt (29.7 mg, 135.12 g/mol, 0.22 mmol, 1 eq) were dissolved in dry DMF/DCM (1/1, 4 ml). After 10 minutes (R)-1-(2-naphthyl)ethylamine (37.7 mg, 171.24 g/mol, 0.22 mmol, 1 eq, Acros) was added to the reaction mixture. After overnight stirring, temperature was raised to 40° C. and kept there for 2 hours. Solvent was then evaporated and residue purified with flash chromatography. 5-(N-Boc-amino)(S)-2-(N'-Fmoc-amino)-N''-((R)-1-(2-naphthyl)ethyl)pentanamide was obtained with quantitative yield.

Step II

Fmoc protection was removed by dissolving the 5-(N-Boc-amino)(S)-2-(N'-Fmoc-amino)-N''-((R)-1-(2-naphthyl)ethyl)pentanamide in 5 ml of 20 vol-% piperidine in DMF. After 45 minutes stirring, solvent and excess of piperidine were evaporated. Product was used without purification for step III.

Step III (S)-2-Amino-5-(N-Boc-amino)-N'-((R)-1-(2-naphthyl)ethyl)pentanamide (0.22 mmol) was dissolved in DMF (1 ml, dry) and 4-methyl-1-naphthalenesulfonyl chloride (53.1 mg, 240.71 g/mol, 0.22 mmol, 1 eq, Maybridge) in THF (1 ml, dry) was added. Finally, TEA (30.5 µl, 101.19 g/mol, 0.73 g/cm$^3$, 0.22 mmol, 1 eq, Baker) was added to the solution. After 15 minutes, some precipitate was observed. After overnight stirring, solvent was evaporated and residue purified with flash chromatography to give 5-(N-Boc-amino)-(S)-2-(N'-(4-methyl-1-naphthalenesulfonyl)amino)-N''-((R)-1-(2-naphthyl)ethyl)pentanamide.

Step IV 5-(N-Boc-amino)-(S)-2-(N'-(4-methyl-1-naphthalenesulfonyl)amino)-N''-((R)-1-(2-naphthyl)ethyl)pentanamide was dissolved in 30% TFA in DCM (3 ml) and mixture was stirred for 45 minutes. After solvent evaporation and flash chromatography 11.4 mg of 5-amino-(S)-2-(N-(4-methyl-1-naphthalenesulfonyl)amino)-N'-((R)-1-(2-naphthyl)ethyl)pentanamide was obtained; overall yield 11%.

MS-ESI$^+$ (m/z): 490

$^1$H NMR (500 MHz, CD$_3$OD; δ, ppm): 8.68 (m, 1H), 8.05-7.94 (m, 2H), 7.84 (m, 1H), 7.77-7.68 (m, 2H), 7.61 (m, 2H), 7.48 (m, 3H), 7.04 (m, 2H), 4.75 (m, 1H), 3.90 (m, 1H), 2.97-2.83 (m, 2H), 2.47 (s, 3H), 1.85-1.62 (m, 4H), 1.15 (d, 3H).

Example 4

Synthesis of 5-amino-N-(2-(3-chlorophenyl)ethyl)-(S)-2-(N'-(4-methyl-1-naphthalenesulfonyl)amino)pentanamide Compound was synthesised according the procedure described in example 3 but (R)-1-(2-naphthyl)ethylamine was substituted with 2-(3-chlorophenyl)ethylamine (30.6 µl, 155.63 g/mol, 1.119 g/cm$^3$, 0.22 mmol, 1 eq). Final Boc deprotection and subsequent flash chromatography gave 73.3 mg of 5-amino-N-(2-(3-chlorophenyl)ethyl)-(S)-2-(N'-(4-methyl-1-naphthalenesulfonyl)amino)pentanamide; yield 68%

MS-ESI$^+$ (m/z): 474

$^1$H NMR (500 MHz, CD$_3$OD; δ, ppm): 8.72 (m, 1H), 8.17 (m, 1H), 8.13 (d, 1H), 7.70 (m, 2H), 7.45 (m, 1H), 7.23-7.15 (m, 2H), 7.03 (m, 1H), 6.92 (m, 1H), 3.68 (m, 1H), 2.93-2.75 (m, 4H), 2.74 (d, 3H), 2.28-2.15 (m, 2H), 1.75-1.52 (m, 4H).

Example 5

Synthesis of 5-amino-N-(1,2-diphenylethyl)-(S)-2-(N'-(4-methyl-1-naphthalenesulfonyl)amino)pentanamide Compound was synthesised according the procedure described in example 3 but (R)-1-(2-naphthyl)ethylamine was substituted with 1,2-diphenylethylamine (42.6 µl, 197.28 g/mol, 1.020 g/cm$^3$, 0.22 mmol, 1 eq). Step I gave 118.1 mg of 5-(N-Boc-amino)-N'-(1,2-diphenylethyl)-(S)-2-(N''-Fmoc-amino)pentanamide; yield 85%. After final Boc deprotection and subsequent flash chromatography, 27.1 mg of 5-amino-N-(1,2-diphenylethyl)-(S)-2-(N'-(4-methyl-1-naphthalenesulfonyl)amino)pentanamide was obtained; yield 28%.

MS-ESI$^+$ (m/z): 516

$^1$H NMR (500 MHz, CD$_3$OD; δ, ppm): 8.75 (m, 1H), 8.67 (m, 1H), 8.21-8.08 (m, 3H), 7.97 (d, 1H), 7.77-7.61 (m, 4H), 7.47 (m, 2H), 7.25-7.05 (m, 12H), 7.00-6.76 (m, 8H), 4.54 (m, 2H), 3.81 (m, 2H), 2.87-2.69 (m, 8H), 2.64 (d, 3H), 2.58 (m, 1H), 2.44 (m, 1H), 2.31 (m, 1H), 1.75-1.31 (m, 8H).

Example 6

Synthesis of 5-amino-N-2-ethoxybenzyl-(S)-2-(N'-(4-methyl-1-naphthalenesulfonyl)amino)pentanamide Compound was synthesised according the procedure described in example 3 but (R)-1-(2-naphthyl)ethylamine was substituted with 2-ethoxybenzylamine (34.1 µl, 151.21 g/mol, 1.015 g/cm$^3$, 0.23 mmol, 1 eq). Step I gave 5-(N-Boc-amino)-N'-2-ethoxybenzyl-(S)-2-(N''-Fmoc-amino)pentanamide with quantitative yield. After final Boc deprotection and subsequent preparative TLC purification, 24 mg of 5-amino-N-2-ethoxybenzyl-(S)-2-(N'-(4-methyl-1-naphthalenesulfonyl)amino)pentanamide was obtained; yield 23%.

MS-ESI⁺ (m/z): 470

$^1$H NMR (500 MHz, CD$_3$OD; δ, ppm): 8.71 (m, 1H), 8.17 (m, 1H), 8.11 (d, 1H), 7.67 (m, 2H), 7.40 (m, 1H), 7.17 (m, 1H), 6.84 (d, 1H), 6.80-6.73 (m, 2H), 3.98 (m, 2H), 3.89 (m, 2H), 3.80 (m, 1H), 2.85-2.72 (m, 5H), 1.70 (m, 2H), 1.60 (m, 2H), 1.35 (t, 3H).

Example 7

Synthesis of 4-amino-N-cyclohexyl-(S)-2-(N'-(4-methyl-1-naphthalenesulfonyl)amino)butanamide (Compound 1)

Compound was synthesised according the procedure described in example 3 but in step I (R)-1-(2-naphthyl)ethylamine was substituted with cyclohexylamine (26 μl, 99.18 g/mol, 0.867 g/cm³, 0.23 mmol, 1 eq) and Fmoc-Orn(Boc)-OH with Fmoc-Dbu(Boc)-OH (100.6 mg, 440.5 g/mol, 0.23 mmol, 1 eq). Step I gave 4-(N-Boc-amino)-N'-cyclohexyl-(S)-2-(N''-Fmoc-amino)butanamide with quantitative yield. After final Boc deprotection and subsequent preparative TLC purification, 34 mg of 4-amino-N-cyclohexyl-(S)-2-(N'-(4-methyl-1-naphthalenesulfonyl)amino)butanamide was obtained; overall yield 37%.

MS-ESI⁺ (m/z): 404

$^1$H NMR (500 MHz, CD$_3$OD; δ, ppm): 8.71 (m, 1H), 8.20 (m, 1H), 8.14 (d, 1H), 7.72 (m, 2H), 7.46 (m, 1H), 3.81 (m, 1H), 3.04 (m, 2H), 2.94 (m, 1H), 2.77 (d, 3H), 1.99 (m, 1H), 1.86 (m, 1H), 1.49 (m, 3H), 1.37 (m, 1H), 1.17-0.94 (m, 4H), 0.58 (m, 1H), 0.45 (m, 1H).

Example 8

Synthesis of 4-amino(S)-2-N-(4-methyl-1-naphthalenesulfonyl)amino-N'-(1-naphthylmethyl)butanamide Step I Fmoc-Dbu(Boc)-OH (100 mg, 440.5 g/mol, 0.23 mmol, 1 eq), DIC (36 μl, 126.20 g/mol, 0.806 g/cm³, 0.23 mmol, 1 eq) and HOBt (31 mg, 135.12 g/mol, 0.23 mmol, 1 eq) were dissolved in dry DMF/DCM (1/1, 3 ml). After 5 minutes 1-naphthylmethylamine (33 μl, 157.22 g/mol, 1.092 g/cm³, 0.23 mmol, 1 eq, Fluka) was added to the reaction mixture. After overnight stirring at 50° C., solvent was evaporated and the residue was dissolved in 30 ml ethyl acetate and washed three times with 20 ml water. Organic phase was dried with Na$_2$SO$_4$ and evaporated. Residue was purified with flash chromatography. 78.5 mg of 4-N-Boc-amino-(S)-2-N'-Fmoc-amino-N''-1-naphthylmethylbutanamide was obtained, yield 60%.

Step II

4-N-Boc-amino-(S)-2-N'-Fmoc-amino-N''-1-naphthylmethylbutanamide was dissolved in 8 ml of 20 vol-% piperidine in DMF. After 45 minutes stirring, solvent and excess of piperidine were evaporated. Residue was used without purification for step III.

Step III (S)-2-Amino-4-N-Boc-amino-N'-(1-naphthylmethyl)butanamide (50.0 mg, 357.46 g/mol, 0.14 mmol, 1 eq) was dissolved in THF (4 ml, dry) and both 4-methyl-1-naphthalenesulfonyl chloride (49 mg, 240.71 g/mol, 0.20 mmol, 1.5 eq, Maybridge) in THF (4 ml, dry) was added. TEA (28 μl, 101.19 g/mol, 0.73 g/cm³, 1.5 eq, Baker) was then added to the solution. After 15 minutes, some precipitate was observed. After overnight stirring, solvent was evaporated and residue purified with flash chromatography.

Step IV

4-N-Boc-amino-(S)-2-N'-(4-methyl-1-naphthalenesulfonyl)amino-N''-(1-naphthylmethyl)butanamide was dissolved in 25% TFA in DCM (5 ml) and mixture was stirred for 30 minutes. Solvent evaporation and subsequent RP-HPLC purification gave 26 mg of 4-Amino-(S)-2-N-(4-methyl-1-naphthalenesulfonyl)amino-N'-(1-naphthylmethyl)butanamide as a white solid, yield 42%.

MS-ESI⁺ (m/z): 462

$^1$H NMR (500 MHz, CD$_3$OD; δ, ppm): 8.67 (m, 1H), 8.13 (m, 1H), 8.08 (d, 1H), 7.86 (d, 1H), 7.78 (d, 1H), 7.72 (d, 1H), 7.63 (m, 2H), 7.48 (m, 1H), 7.42 (m, 1H), 7.32 (m, 2H), 7.06 (d, 1H), 4.44 (d, 1H), 4.27 (d, 1H), 3.90 (m, 1H), 2.97 (m, 1H), 2.87 (m, 1H), 2.73 (s, 3H), 2.01 (m, 1H), 1.89 (m, 1H).

Example 9

Synthesis of 4-amino-N-2-(3-chlorophenyl)ethyl-(S)-2-(N'-(4-methyl-1-naphthalenesulfonyl)amino)butanamide Step I Fmoc-Dbu(Boc)-OH (250.8 mg, 440.5 g/mol, 0.57 mmol, 1 eq), DIC (89 μl, 126.20 g/mol, 0.806 g/cm³, 0.57 mmol, 1 eq) and HOBt (77.6 mg, 135.12 g/mol, 0.57 mmol, 1 eq) were dissolved in dry DMF/DCM (1/1, 6 ml). After 5 minutes 2-(3-chlorophenyl)ethylamine (79 μl, 155.63 g/mol, 1.119 g/cm³, 0.57 mmol, 1 eq) was added to the reaction mixture. Temperature was raised to 35° C. and mixture stirred overnight. Solvent was then evaporated and residue dissolved in DCM, which was washed twice with water and once with brine. Organic phase was subsequently dried with Na$_2$SO$_4$ and evaporated. Residue was purified with silica column chromatography (mobile phase starting from DCM up to 5% MeOH in DCM). 4-(N-Boc-amino)-N'-2-(3-chlorophenyl)ethyl-(S)-2-(N''-Fmoc-amino)butanamide was obtained with quantitative yield.

Step II

Fmoc protection was removed by dissolving the 4-(N-Boc-amino)-N'-2-(3-chlorophenyl)ethyl-(S)-2-(N''-Fmoc-amino)butanamide in 5 ml of 20 vol-% piperidine in DMF. After 30 minutes stirring, solvent and excess of piperidine were evaporated. Product was used without purification for step III.

Step III (S)-2-Amino-4-(N-Boc-amino)-N'-(2-(3-chlorophenyl)ethyl)butanamide (0.57 mmol) was dissolved in DMF (3 ml, dry) and 4-methyl-1-naphthalenesulfonyl chloride (206 mg, 240.71 g/mol, 0.86 mmol, 1.5 eq, Maybridge) in THF (3 ml, dry) was added. Finally, TEA (119 μl, 101.19 g/mol, 0.73 g/cm³, 0.86 mmol, 1.5 eq, Baker) was added to the solution. After 15 minutes, some precipitate was observed. After overnight stirring, solvent was evaporated and residue purified with silica column chromatography (mobile phase 5% MeOH in DCM) to give 220 mg of 4-(N-Boc-amino)-N'-(2-(3-chlorophenyl)ethyl)-(S)-2-(N''-(4-methyl-1-naphthalenesulfonyl)amino)butanamide, yield 67%.

Step IV 4-(N-Boc-amino)-N'-(2-(3-chlorophenyl)ethyl)-(S)-2-(N''-(4-methyl-1-naphthalenesulfonyl)amino)butanamide (220 mg, 560.11 g/mol, 0.39 mmol) was dissolved in 25% TFA in DCM (10 ml) and mixture was stirred for 45 minutes.

After solvent evaporation and silica column chromatography (mobile phase from DCM up to 10% MeOH in DCM) 163 mg of 4-amino-N-2-(3-chlorophenyl)ethyl-(S)-2-(N'-(4-methyl-1-naphthalenesulfonyl)amino)butanamide was obtained; yield 91%.

MS-ESI⁺ (m/z): 460

¹H NMR (500 MHz, CD₃OD; δ, ppm): 8.72 (m, 1H), 8.18 (m, 1H), 8.14 (d, 1H), 7.76-7.67 (m, 2H), 7.46 (m, 1H), 7.22-7.15 (m, 2H), 7.03 (t, 1H), 6.91 (m, 1H), 3.76 (m, 1H), 2.99-2.84 (m, 3H), 2.83-2.73 (m, 4H), 2.22 (m, 2H), 1.89 (m, 1H), 1.79 (m, 1H).

Example 10

Synthesis of 5-amino-N-benzyl-(S)-2-(N'-(4-methyl-1-naphthalenesulfonyl)amino)pentanamide Step I Fmoc-Orn(Boc)-OH (250.9 mg, 454.5 g/mol, 0.55 mmol, 1 eq), DIC (86 µl, 126.20 g/mol, 0.806 g/cm³, 0.55 mmol, 1 eq) and HOBt (74.2 mg, 135.12 g/mol, 0.55 mmol, 1 eq) were dissolved in dry DMF/DCM (1/1, 6 ml). After 5 minutes benzylamine (60 µl, 107.16 g/mol, 0.981 g/cm³, 0.55 mmol, 1 eq) was added to the reaction mixture. Temperature was raised to 35° C. and mixture stirred overnight. Solvent was then evaporated and residue dissolved in DCM, which was washed twice with water and once with brine. Organic phase was subsequently dried (Na₂SO₄) and evaporated. Residue was purified with silica column chromatography (mobile phase from DCM up to 10% MeOH in DCM). N-Benzyl-5-N'-Boc-amino-(S)-2-(N''-Fmoc-amino)pentanamide was obtained with quantitative yield.

Step II

Fmoc protection was removed by dissolving the N-benzyl-5-N'-Boc-amino-(S)-2-(N''-Fmoc-amino)pentanamide in 5 ml 20 vol-% piperidine in DMF. After 1.5 hours stirring, solvent and excess of piperidine were evaporated. Product was used without purification for step III.

Step III (S)-2-Amino-N-benzyl-5-(N'-Boc-amino)pentanamide (0.55 mmol) was dissolved in DMF (2.5 ml, dry) and 4-methyl-1-naphthalenesulfonyl chloride (200 mg, 240.71 g/mol, 0.83 mmol, 1.5 eq, Maybridge) in THF (2.5 ml, dry) was added. Finally, TEA (115 µl, 101.19 g/mol, 0.73 g/cm³, 0.83 mmol, 1.5 eq, Baker) was added to the solution. After 15 minutes, some precipitate was observed. After overnight stirring, solvent was evaporated and residue purified with silica column chromatography (mobile phase 10% MeOH in DCM) to give N-benzyl-5-(N'-Boc-amino)-(S)-2-(N''-(4-methyl-1-naphthalenesulfonyl)amino)pentanamide with quantitative yield.

Step IV

N-Benzyl-5-(N'-Boc-amino)-(S)-2-(N''-(4-methyl-1-naphthalenesulfonyl)amino)pentanamide (289 mg, 525.67 g/mol, 0.55 mmol) was dissolved in 25% TFA in DCM (10 ml) and mixture was stirred for 1 hour. After solvent evaporation and RP-HPLC purification, 96.6 mg of 5-amino-N-benzyl-(S)-2-(N'-(4-methyl-1-naphthalenesulfonyl)amino)pentanamide was obtained; yield 41%.

MS-ESI⁺ (m/z): 426

¹H NMR (500 MHz, CD₃OD; δ, ppm): 8.81 (m, 1H), 8.27 (m, 1H), 8.19 (d, 1H), 7.77 (m, 2H), 7.49 (d, 1H), 7.28 (m, 3H), 6.99 (m, 2H), 3.94 (d, 2H), 3.87 (m, 1H), 2.91 (m, 2H), 2.85 (s, 3H), 1.80 (m, 2H), 1.71 (m, 2H).

Example 11

Synthesis of 4-amino-N-(S)-1-carbamoyl-2-phenyl-ethyl-(S)-2-(N'-(4-methyl-1-naphthalenesulfonyl) amino)butanamide (Compound 2)

Step I

H-Phe-NH₂ hydrochloride (114.2 mg, 200.7 g/mol, 0.57 mmol, 1 eq, Advanced ChemTech) was dissolved in 2 ml of dry DMF/DCM (1/1) and TEA (95 µl, 101.19 g/mol, 0.73 g/cm³, 0.68 mmol, 1.2 eq) was added. After 30 minutes, a DMF/DCM (1/1, 4 ml) solution containing Fmoc-Dbu(Boc)-OH (250.2 mg, 440.5 g/mol, 0.57 mmol, 1 eq), DIC (89 µl, 126.20 g/mol, 0.805 g/cm³, 0.57 mmol, 1 eq) and HOBt (77.6 mg, 135.12 g/mol, 0.57 mmol, 1 eq) was added. After overnight stirring, solvent was evaporated and DCM (30 ml) was added. Organic phase was washed three times with water (10 ml) and once with brine (10 ml). Part of the product precipitated from the water phase and after filtration it was combined with the evaporated organic phase. 333 mg of 4-(N-Boc-amino)-N'-((S)-1-carbamoyl-2-phenylethyl)-(S)-2-(N''-Fmoc-amino)butanamide was obtained as a white powder with quantitative yield.

Step II

Fmoc protection was removed by treating the 4-(N-Boc-amino)-N'-((S)-1-carbamoyl-2-phenylethyl)-(S)-2-(N''-Fmoc-amino)butanamide with 4.5 ml of 20 vol-% piperidine in DMF for 45 minutes. Solvent was then evaporated to give (S)-2-amino-4-(N-Boc-amino)-N'-((S)-1-carbamoyl-2-phenylethyl)butanamide as a white solid.

Step III

Residue from step II was dissolved in 9 ml of dry THF/DMF (1/1) solution and 4-methyl-1-naphthalenesulfonyl-chloride (205.3 mg, 240.71 g/mol, 0.85 mmol, 1.5 eq, Maybridge) and finally TEA (120 µl, 101.19 g/mol, 0.73 g/cm³, 0.85 mmol, 1.5 eq, Baker) were added. After overnight reaction, solvent was evaporated and the residue purified with silica column chromatography (mobile phase from 5% MeOH in DCM up to 20% MeOH in DCM). 238 mg of 4-(N-Boc-amino)-N'-((S)-1-carbamoyl-2-phenylethyl)-(S)-2-(N''-(4-methyl-1-naphthalenesulfonyl)amino)butanamide as a white powder was obtained; yield 75%.

Step IV

Boc protection was remove by dissolving the product from step III in 2.5 ml of 25 vol-% TFA in DCM and stirring for 1 h. Solvent was then evaporated and residue purified with RP-HPLC to give 52.5 mg of 4-amino-N-(S)-1-carbamoyl-2-phenylethyl-(S)-2-(N'-(4-methyl-1-naphthalenesulfonyl) amino)butanamide; yield 26.8%.

MS-ESI⁺ (m/z): 469

¹H NMR (500 MHz, CD₃OD; δ, ppm): 8.69 (m, 1H), 8.16 (m, 1H), 8.07 (m, 1H), 7.69 (m, 2H), 7.39 (d, 1H), 7.25-7.16 (m, 3H), 7.06 (m, 2H), 4.21 (t, 1H), 3.84 (m, 1H), 2.84-2.69 (m, 6H), 2.49 (m, 1H), 1.94-1.74 (m, 2H).

Example 12

Synthesis of 4-amino-N-benzyl-(S)-2-(N'-(4-methyl-1-naphthalenesulfonyl)amino)butanamide Step I Fmoc-Dbu(Boc)-OH (1.00 g, 440.5 g/mol, 2.27 mmol, 1 eq), DIC (355 µl, 126.20 g/mol, 0.806 g/cm³, 2.27 mmol, 1 eq) and HOBt (308.2 mg, 135.12 g/mol, 2.27 mmol, 1 eq)

were dissolved in dry DMF/DCM (1/1, 10 ml). After 5 minutes, benzylamine (248 µl, 107.16 g/mol, 2.27 mmol, 1 eq, Acros) was added to the reaction mixture and temperature raised to 35° C. After overnight stirring, solvent was evaporated and residue dissolved in DCM and washed twice with water and once with brine. Organic phase was dried with $Na_2SO_4$ and solvent evaporated. Residue was purified with silica column chromatography (mobile phase from DCM up to 5% MeOH in DCM). N-Benzyl-4-(N'-Boc-amino)-(S)-2-(N"-Fmoc-amino)butanamide was obtained with quantitative yield.

Step II

Fmoc protection was removed by dissolving the N-benzyl-4-(N'-Boc-amino)-(S)-2-(N"-Fmoc-amino)butanamide (1.12 g, 529.64 g/mol, 2.1 mmol, 1 eq) in 10 ml 20 vol-% piperidine in DMF. After 1.5 hours stirring, solvent and excess of piperidine were evaporated. Product was used without purification for step III.

Step III (S)-2-Amino-N-benzyl-4-(N'-Boc-amino)butanamide (2.1 mmol) was dissolved in THF (7 ml, dry) and 4-methyl-1-naphthalenesulfonyl chloride (761 mg, 240.71 g/mol, 3.15 mmol, 1.5 eq, Maybridge) was added. Finally, TEA (440 µl, 101.19 g/mol, 0.73 g/cm$^3$, 3.15 mmol, 1.5 eq, Baker) was added to the solution. After 15 minutes, some precipitate was observed. After overnight stirring, solvent was evaporated and residue purified with silica column chromatography (mobile phase 5% MeOH in DCM) to give 860 mg of N-benzyl-4-(N'-Boc-amino)-(S)-2-((4-methyl-1-naphthalene)amino) butanamide; yield 80%.

Step IV

N-Benzyl-4-(N'-Boc-amino)-(S)-2-((4-methyl-1-naphthalene)amino)butanamide (850 mg, 511.64 g/mol, 1.66 mmol) was dissolved in 25% TFA in DCM (10 ml) and mixture was stirred for 1 hour. After solvent evaporation and silica column chromatography 4-amino-N-benzyl-(S)-2-(N'-(4-methyl-1-naphthalenesulfonyl)amino)butanamide was obtained with quantitative yield.

MS-ESI$^+$ (m/z): 412

$^1$H NMR (500 MHz, CD$_3$OD; δ, ppm): 8.69 (m, 1H), 8.16 (m, 1H), 8.10 (d, 1H), 7.66 (m, 2H), 7.39 (d, 1H), 7.17 (m, 3H), 6.88 (m, 2H), 3.88 (d, 2H), 3.84 (m, 1H), 2.91 (m, 1H), 2.82 (m, 1H), 2.74 (s, 3H), 1.96 (m, 1H), 1.83 (m, 1H).

Example 13

Synthesis of N-benzyl-4-(N',N'-dicyclopropyl)amino-(S)-2-(N"-(4-methyl-1-naphthalenesulfonyl)amino)butanamide Step I 4-Amino-N-benzyl-(S)-2-(N'-(4-methyl-1-naphthalenesulfonyl)amino)butanamide (45.9 mg, 411.52 g/mol, 0.11 mmol) prepared in example 12 was dissolved in dry MeOH and acetic acid (32 µl, 60.05 g/mol, 1.05 g/cm$^3$, 0.55 mmol, 5 eq, Acros) and molecular sieves (3 Å) were added. Finally, (1-ethoxycyclopropoxy)trimethylsilane (66 µl, 173.42 g/mol, 0.867 g/cm$^3$, 0.33 mmol, 3 eq, Acros) and sodium cyanoborohydride (18 mg, 62.84 g/mol, 0.28 mmol, 2.5 eq, Acros) were added. Mixture was refluxed overnight, molecular sieves filtered and the filtrate evaporated. Residue was dissolved in ethyl acetate and washed with saturated NaHCO$_3$ and water. Organic phase was then dried with Na$_2$SO$_4$ and evaporated. Residue was purified with preparative TLC (10% MeOH in DCM as mobile phase) and 7 mg of N-benzyl-4-(N',N'-dicyclopropyl)amino-(S)-2-(N"-(4-methyl-1-naphthalenesulfonyl)amino)butanamide was obtained; yield 13%.

MS-ESI$^+$ (m/z): 492

$^1$H NMR (500 MHz, CD$_3$OD; δ, ppm): 8.75 (m, 1H), 8.18 (m, 1H), 8.13 (d, 1H), 7.69 (m, 2H), 7.43 (m, 1H), 7.28-7.18 (m, 3H), 7.10 (m, 2H), 4.07 (d, 2H), 3.70 (m, 1H), 2.76 (d, 3H), 2.40 (m, 1H), 2.30 (m, 1H), 1.90 (m, 1H), 1.73 (m, 1H), 1.55 (m, 2H), 0.30-0.13 (m, 8H).

Example 14

Synthesis of N-benzyl-4-(N'-isopropyl)amino-(S)-2-(N"-(4-methyl-1-naphthalenesulfonyl)amino)butanamide (Compound 3)

4-Amino-N-benzyl-(S)-2-(N'-(4-methyl-1-naphthalenesulfonyl)amino)butanamide (50.0 mg, 411.52 g/mol, 0.12 mmol) prepared in example 12 was dissolved in TMOF and acetone (8.8 µl, 58.08 g/mol, 0.79 g/cm$^3$, 0.12 mmol, 1 eq, Prolabo), acetic acid (10.3 µl, 60.05 g/mol, 1.05 g/cm$^3$, 0.18 mmol, 1.5 eq, Acros) and finally sodium triacetoxyborohydride (39 mg, 211.94 g/mol, 0.18 mmol, 1.5 eq, Acros) were added. Mixture was stirred for 2 hours and additional 0.5 eq of acetone was added. After overnight stirring, solvent was evaporated. The residue was dissolved in ethyl acetate and washed with water. After drying with Na$_2$SO$_4$, the organic phase was evaporated. Product was purified with preparative TLC (10% MeOH in DCM as mobile phase) and 18 mg of N-benzyl-4-(N'-isopropyl)amino-(S)-2-(N"-(4-methyl-1-naphthalenesulfonyl)amino)butanamide was obtained, yield 33%.

MS-ESI$^+$ (m/z): 454

$^1$H NMR (500 MHz, CD$_3$OD; δ, ppm): 8.72 (m, 1H), 8.20 (m, 1H), 8.14 (d, 1H), 7.70 (m, 2H), 7.44 (m, 1H), 7.24-7.19 (m, 3H), 6.97 (m, 2H), 4.00 (m, 2H), 3.87 (m, 1H), 3.11 (m, 1H), 2.83 (m, 1H), 2.77 (s, 3H), 2.73 (m, 1H), 1.98 (m, 1H), 1.85 (m, 1H), 1.16 (m, 6H).

Example 15

Synthesis of N-benzyl-4-guanidino-(S)-2-(N'-(4-methyl-1-naphthalenesulfonyl)amino)butanamide (Compound 4)

Step I

4-Amino-N-benzyl-(S)-2-(N'-(4-methyl-1-naphthalenesulfonyl)amino)butanamide (123 mg, 451.59 g/mol, 0.27 mmol, 1 eq) prepared in example 12 was dissolved in 4 ml of dry DCM under argon and TEA (190 µl, 101.19 g/mol, 0.73 g/cm$^3$, 0.82 mmol, 3 eq, Baker) was added to the solution. N,N'-Bis(tertbutoxycarbonyl)-N"-triflylguanidine (273 mg, 391.4 g/mol, 0.41 mmol, 1.5 eq) was dissolved in DCM (1 ml) and added dropwise to the reaction mixture. After 18 h stirring, solvent was evaporated and purified with silica column chromatography (mobile phase from DCM up to 2.5% MeOH in DCM) to give 250 mg of N-benzyl-4-(N',N"-diBoc-guanidino)-(S)-2-(N'"-(4-methyl-1-naphthalenesulfonyl)amino)butanamide, yield 83%.

Step II

Boc protections were removed by dissolving the product after step I in 25 vol-% TFA in DCM (10 ml) and the mixture was stirred for 1 hour. Subsequent solvent evaporation and flash chromatographic purification gave 172 mg of N-benzyl- 4-guanidino-(S)-2-(N'-(4-methyl-1-naphthalenesulfonyl)
amino)butanamide with quantitative yield.

MS-ESI⁺ (m/z): 454

¹H NMR (500 MHz, CD₃OD; δ, ppm): 8.73-8.71 (m, 1H),
8.20-8.18 (m, 1H), 8.13-8.11 (m, 1H), 7.76-7.71 (m, 2H),
7.41-7.39 (m, 1H), 7.22-7.20 (m, 3H), 6.93-6.70 (m, 2H),
4.00-3.95 (m, 2H), 3.85-3.82 (m, 1H), 3.19-3.07 (m, 2H),
2.76 (s, 3H), 1.93-1.87 (m, 1H) 1.77-1.70 (m, 1H).

Example 16

Synthesis of 5-N-methylamino-(S)-2-(N'-(1-naphthalenesulfonyl)amino)-N''-phenylpentanamide Step I Boc-Orn(2-Cl—Z)-OH (1.0 g, 400.86 g/mol, 2.5 mmol, 1
eq), DIC (390 μl, 126.20 g/mol, 0.806 g/cm³, 2.5 mmol, 1 eq)
and HOBt (339.7 mg, 135.12 g/mol, 2.5 mmol, 1 eq) were
dissolved in dry DMF (5 ml). After 5 minutes, aniline (228 μl,
93.13 g/mol, 1.022 g/cm³, 2.5 mmol, 1 eq) in dry DCM (5 ml)
was added. Temperature was raised to 35° C. and solution
stirred overnight. Solution was then evaporated, DCM added
and solution washed twice with water and once with brine.
Organic phase was dried with Na₂SO₄ and evaporated. Subsequent silica column chromatography (2% MeOH in DCM
as mobile phase) gave 1.12 g of 5-N-(2-Cl—Z)amino-(S)-2-
(N'-Boc-amino)-N''-phenylpentanamide, yield 94%.

Step II

2-Cl—Z protection was removed by dissolving the product
from step I in MeOH (60 ml) and 10% Pd/C (200 mg) was
added. Reaction vessel was flushed thrice with argon before
introduction of hydrogen (atmospheric pressure). Mixture
was stirred for 4 h, catalyst filtered and finally filtrate evaporated. 5-Amino-(S)-2-(N-Boc-amino)-N'-phenylpentanamide was used without purification for step III.

Step III

5-Amino-(S)-2-(N-Boc-amino)-N'-phenylpentanamide
(720 mg, 307.39 g/mol, 2.34 mmol, 1 eq) was dissolved in dry
DMF (5 ml), TEA (324 μl, 101.19 g/mol, 0.73 g/cm³, 2.34
mmol, 1 eq, Baker) added and the mixture cooled in an ice
bath. 2-Nitrobenzenesulfonyl chloride (520.7 mg, 221.62
g/mol, 2.34 mmol, 1 eq) in dry DCM (1 ml) was added, ice
bath removed and solution stirred overnight. Solvent was then
evaporated, DCM added and solution washed twice with saturated NaHCO₃ and once with water. Organic phase was dried
(Na₂SO₄), evaporated and finally the residue was purified
with silica column chromatography (mobile phase 2.5%
MeOH in DCM). 440 mg of (S)-2-(N-Boc-amino)-5-N'-(2-
nitrobenzenesulfonyl)amino)-N''-phenylpentanamide was
obtained, yield 38%.

Step IV (S)-2-(N-Boc-amino)-5-N'-(2-nitrobenzenesulfonyl)
amino)-N''-phenylpentanamide (200.8 mg, 492.55 g/mol,
0.41 mmol, 1 eq) was dissolved in dry DMF (0.5 ml) and
DBU (61 μl, 152.24 g/mol, 1.018 g/cm³, 0.41 mmol, 1 eq,
Acros) was added. Solution was then cooled in an ice bath and
methyl iodide (25 μl, 141.94 g/mol, 2.28 g/cm³, 0.41 mmol, 1
eq) added dropwise. Cooling was removed and mixture
stirred overnight. Additional 0.5 eq of methyl iodide and
DBU was added and after 2 hours yet another 0.5 eq of methyl
iodide and DBU. After 2 hours, solvent was evaporated, DCM
added and solution washed twice with saturated NaHCO₃ and
once with water. Organic phase was dried (Na₂SO₄) and
evaporated. After preparative TLC purification 135 mg of
(S)-2-(N-Boc-amino)-5-(N'-2-nitrobenzenesulfonyl-N'-methylamino)-N''-phenylpentanamide was obtained, yield 65%.

Step V

Boc protection was removed by dissolving the product
after step IV in 3 ml of 25 vol-% TFA in DCM and stirring the
solution for 45 minutes. Solvent was then evaporated and
product used without purification for step VI.

Step VI (S)-2-Amino-5-(N-2-nitrobenzenesulfonyl-N-methylamino)-N'-phenylpentanamide (100 mg, 406.46 g/mol, 0.25
mmol, 1 eq) was dissolved in dry THF (3 ml), 1-naphthalenesulfonyl chloride (67.4 mg, 226.68 g/mol, 0.30 mml, 1.2
eq) and finally TEA (87 μl, 101.19 g/mol, 0.73 g/cm³, 0.63
mmol, 2.5 eq, Baker) were added. After overnight stirring, 0.2
eq of 1-naphthalenesulfonyl chloride and 1 eq of TEA were
added and reaction temperature raised to 50° C. After additional 1.5 hours, solvent was evaporated and residue purified
with silica column chromatography (mobile phase 2% MeOH
in DCM). 138 mg of (S)-2-(N-1-naphthalenesulfonylamino)-
5-(N'-2-nitrobenzenesulfonyl-N'-methylamino)-N''-phenylpentanamide was obtained, yield 93%.

Step VII (S)-2-(N-1-Naphthalenesulfonylamino)-5-(N'-2-nitrobenzenesulfonyl-N'-methylamino)-N''-phenylpentanamide (67
mg, 596.69 g/mol, 0.11 mmol, 1 eq) was dissolved in dry
DMF (0.5 ml) and a solution containing thiophenol (115 μl,
110.18 g/mol, 1.078 g/cm³, 1.1 mmol, 10 eq), K₂CO₃ (40.4
mg, 138.21 g/mol, 0.28 mmol, 2.5 eq, Baker) and water
(200 μl) was added. Finally, TEA (155 μl, 101.19 g/mol, 0.73
g/cm³, 1.1 mmol, 10 eq, Baker) was added and temperature
raised to 50° C. After 1.5 hours, solvent was evaporated,
DCM added and solution washed twice with water and once
with brine. Organic phase was dried (Na₂SO₄) and evaporated. Flash chromatography gave 18.4 mg of 5-N-methylamino-(S)-2-N'-(1-naphthalenesulfonyl)amino)-N''-phenylpentanamide; yield 41%.

MS-ESI⁺ (m/z): 412

¹H NMR (500 MHz, CD₃OD; δ, ppm): 8.78 (m, 1H), 8.22
(m, 1H), 7.98 (d, 1H), 7.90 (d, 1H), 7.68 (m, 1H), 7.57 (m,
1H), 7.46 (m, 1H), 7.13 (m, 2H), 7.03-6.96 (m, 3H), 3.82 (m,
1H), 2.42 (m, 2H), 2.28 (s, 3H), 1.64 (m, 2H), 1.52 (m, 1H),
1.40 (m, 1H).

Example 17

Synthesis of N-((S)-1-carbamoyl-2-phenylethyl)-5-
guanidino-(S)-2-(N'-(4-methyl-1-naphthalenesulfonyl)amino)pentanamide (Compound 5)

Step I

Rink amide resin (1 g, 0.7 mmol/g, 0.7 mmol) was washed
twice with DMF prior use. Washed resin was dissolved in
12.5 ml of 20 vol-% piperidine in DMF and mixture was
agitated for 35 minutes. Resin was then washed thrice with
DMF, thrice with MeOH, twice with DCM and finally twice
with THF. Resin was used immediately for step II.

Step II

Fmoc-Phe-OH (813.6 mg, 387.44 g/mol, 2.1 mmol, 3 eq)
and DIC (328.8 μl, 126.20 g/mol, 0.806 g/cm³, 2.1 mmol, 3
eq) were dissolved in dry DMF (12.5 ml) and after 10 minutes
mixed with the resin. After 18 hours agitation, solvent was
filtered out and fresh solution with half of the original
amounts of Fmoc-Phe-OH and DIC in dry DMF was introduced. After additional 5.5 hours, solvent was again filtered out and resin washed thrice with DMF, thrice with MeOH, thrice with DCM and thrice with THF.

Step III
Possibly unreacted amino groups of the resin were acetylated with a solution consisting of acetic anhydride (1 ml, 102.09 g/mol, 1.087 g/cm$^3$, 10.6 mmol) and DIPEA (250 μl, 129.25 g/mol, 0.755 g/cm$^3$, 1.46 mmol) in dry DMF (12 ml) for 45 minutes. Resin was then filtered and washed thrice with DMF, thrice with MeOH, twice with DCM and twice with THF.

Step IV
Fmoc protection of the attached phenylalanine was removed according to procedure described in step I but without any washes prior treatment with piperidine/DMF.

Step V
Fmoc-Arg(Pmc)-OH (928.0 mg, 662.8 g/mol, 1.4 mmol, 2 eq) was coupled to resin bound compound using the same coupling agent and procedure as described in step II.

Step VI
Possibly unreacted amino groups of phenylalanine were acetylated using the procedure described in step III.

Step VII
Fmoc protection of the arginine attached in step V was removed according to procedure described in step I but again without any washes prior treatment with piperidine/DMF.

Step VIII
4-Methyl-1-naphthalenesulfonyl chloride (337.0 mg, 240.71 g/mol, 1.4 mmol, 2 eq, Maybridge) was dissolved in dry THF (12.5 ml) and mixed with the resin. TEA (194.1 μl, 101.19 g/mol, 0.73 g/cm$^3$, 1.4 mmol, 2 eq, Baker) was then added to the mixture. After overnight agitation, solvent was filtered and resin washed thrice with THF, thrice with MeOH, thrice with DMF, once with MeOH and finally thrice with DCM.

Step IX
Resin bound product was cleaved and Pmc protection removed by treating the resin with 50 vol-% TFA in DCM (12.5 ml) for 1 hour. Resulting red solution was collected and evaporated. 116.5 mg of N-((S)-1-carbamoyl-2-phenylethyl)-5-guanidino-(S)-2-(N'-(4-methylnaphthalene-1-sulfonyl)amino)pentanamide as a dark oil was obtained. Product was purified using flash chromatography to give 50.8 mg of N-((S)-1-carbamoyl-2-phenylethyl)-5-guanidino-(S)-2-(N'-(4-methyl-1-naphthalenesulfonyl)amino)pentanamide as white solid, overall yield 14%.

MS-ESI$^+$ (m/z): 525
$^1$H NMR (500 MHz, CD$_3$OD; δ, ppm): 8.79 (m, 1H), 8.23 (m, 1H), 8.14 (d, 1H), 7.76 (m, 2H), 7.47 (m, 1H), 7.33-7.18 (m, 5H), 4.39 (m, 1H), 3.62 (m, 1H), 3.03 (m, 1H), 2.94-2.78 (m, 5H), 2.68 (m, 1H), 1.50 (m, 2H), 1.35 (m, 1H), 1.21 (m, 1H).

Example 18

Synthesis of 5-amino-N-((S)-1-carbamoylmethyl-2-(1-naphthyl)ethyl)-(S)-2-(N'-(4-methyl-1-benzenesulfonyl)amino)pentanamide Step I
Rink amide resin (200.2 mg, 0.7 mmol/g, 0.14 mmol) was washed twice with DMF prior use. Washed resin was dissolved in 2.5 ml of 20 vol-% piperidine in DMF and mixture was agitated for 30 minutes. Resin was then washed thrice with DMF, twice with MeOH, twice with DCM and finally twice with THF. Resin was used immediately for step II.

Step II
Fmoc-(S)-3-amino-4-(naphthyl)butyric acid (124 mg, 451.52 g/mol, 0.28 mmol, 2 eq, PepTech) and DIC (44 μl, 126.20 g/mol, 0.806 g/cm$^3$, 0.28 mmol, 2 eq) were dissolved in dry DMF and after 5 minutes mixed with the resin. After 6 hours, solvent was filtered out and fresh solution with same amounts of Fmoc-(S)-3-amino-4-(naphthyl)butyric acid and DIC in dry DMF were introduced. After additional 6 hours, solvent was again filtered out and resin washed twice with DMF, twice with MeOH, once with DCM and once with THF.

Step III
Possibly unreacted amino groups were acetylated by treating the resin with a solution consisting of acetic anhydride (100 μl, 102.09 g/mol, 1.087 g/cm$^3$, 1.06 mmol) and DIPEA (17 μl, 129.25 g/mol, 0.755 g/cm$^3$, 0.1 mmol) in dry DMF (2.1 ml) for 30 minutes. Resin was then filtered and washed twice with DMF, twice with MeOH, once with DCM and once with THF.

Step IV
Fmoc protection of the attached Fmoc-(S)-3-amino-4-(naphthyl)butyric acid was removed according to procedure described in step I but without any washes prior treatment with piperidine/DMF.

Step V
Fmoc-Orn(Boc)-OH (197.5 mg, 454.5 g/mol, 0.44 mmol, 3 eq) was coupled to resin bound compound using the same coupling agent and procedure as described in step II.

Step VI
Possibly unreacted amino groups were acetylated using the procedure described in step III.

Step VII
Fmoc protection of the ornithine attached in step V was removed according to procedure described in step I but without any washes prior treatment with piperidine/DMF.

Step VIII
4-Toluenesulfonyl chloride (80 mg, 190.65 g/mol, 0.42 mmol, 3 eq) was dissolved in dry THF (2.5 ml), mixed with the resin and TEA (58 μl, 101.19 g/mol, 0.73 g/cm$^3$, 0.42 mmol, 3 eq, Baker) was added to the mixture. After overnight agitation, solvent was filtered and resin washed thrice with THF, twice with MeOH, twice with DMF, once with MeOH and finally thrice with DCM.

Step IX
Resin bound product was cleaved and Boc protection removed by treating the resin with 25 vol-% TFA in DCM (2.5 ml) for 45 minutes. Resulting red solution was collected and evaporated. Residue was purified with RP-HPLC to give 12 mg of 5-amino-N-((S)-1-carbamoylmethyl-2-(1-naphthyl)ethyl)-(S)-2-(N'-(4-methyl-1-benzenesulfonyl)amino)pentanamide as white solid, overall yield 17%.

MS-ESI$^+$ (m/z): 497
$^1$H NMR (500 MHz, CD$_3$OD; δ, ppm): 8.15-8.07 (m, 1H), 7.90-7.86 (m, 1H), 7.77-7.76 (m, 1H), 7.71-7.69 (m, 1H), 7.55-7.48 (m, 2H), 7.40-7.37 (m, 1H), 7.29-7.21 (m, 3H), 4.37-4.31 (m, 1H), 3.79-3.77 (m, 1H), 3.35-3.34 (m, 2H), 2.97-2.80 (m, 4H), 2.28-2.19 (m, 1H), 2.15 (m, 3H), 1.69-1.54 (m, 3H).

Example 19

Synthesis of N-((S)-1-carbamoyl-2-phenylethyl)-6-guanidino-(S)-3-(N'-(1-naphthalenesulfonyl)amino)hexanamide Step I Rink amide resin (208.6 mg, 0.7 mmol/g, 0.15 mmol) was washed twice with DMF prior use. Washed resin was dissolved in 2.5 ml of 20 vol-% piperidine in DMF and mixture was agitated for 30 minutes. Resin was then washed thrice with DMF, twice with MeOH, twice with DCM and finally twice with THF. Resin was used immediately for step II.

Step II

Fmoc-Phe-OH (114.9 mg, 387.44 g/mol, 0.30 mmol, 2 eq) was coupled to the resin using the same procedure and coupling agent as described in step II of example 18.

Step III

Possibly unreacted amino groups were acetylated using the procedure described in step III in example 18.

Step IV

Fmoc protection of the attached phenylalanine was removed according to procedure described in step I but without any washes prior treatment with piperidine/DMF.

Step V

N-Fmoc-L-beta-homo-arginine(Pbf)-OH (281.0 mg, 662.8 g/mol, 0.42 mmol, 3 eq) was coupled to resin bound compound using the same coupling agent and procedure as described in step II in example 18.

Step VI

Possibly unreacted amino groups were acetylated using the procedure described in step III in example 18.

Step VII

Fmoc protection of the attached beta-homo-arginine was removed according to procedure described in step I but without any washes prior treatment with piperidine/DMF.

Step VIII

1-Naphthalenesulfonyl chloride (78.5 mg, 226.7 g/mol, 0.34 mmol, 2.5 eq, Acros) was introduced according to the procedure described in step VIII of example 18.

Step IX

Resin bound product was cleaved and Pbf protection removed by treating the resin with 40 vol-% TFA in DCM (2.5 ml) for 45 minutes. Resulting red solution was collected and evaporated. Residue was purified with RP-HPLC to give 14.9 mg of N-((S)-1-carbamoyl-2-phenylethyl)-6-guanidino-(S)-3-(N'-(1-naphthalenesulfonyl)amino)hexanamide as white solid, overall yield 19%.

MS-ESI$^+$ (m/z): 525

$^1$H NMR (500 MHz, CD$_3$OD; δ, ppm): 8.65-8.63 (m, 1H), 8.25-8.23 (m, 1H), 8.15-8.13 (m, 1H), 7.93-7.92 (m, 1H), 7.69-7.56 (m, 3H), 7.24-7.14 (m, 5H), 4.53-4.48 (m, 1H), 3.45-3.41 (m, 1H), 3.12-3.08 (m, 1H), 2.78-2.67 (m, 3H), 2.19-2.15 (m, 1H), 2.03-1.98 (m, 1H), 1.26-0.95 (m, 4H).

Example 20

Synthesis of 6-amino-(S)-2-(N-benzenesulfonylamino)-N'-((S)-1-carbamoyl-2-(1H-indol-3-yl)ethyl)hexanamide Step I Rink amide resin (205.8 mg, 0.7 mmol/g, 0.14 mmol) was washed twice with DMF prior use. Washed resin was dissolved in 2.5 ml of 20 vol-% piperidine in DMF and mixture was agitated for 30 minutes. Resin was then washed thrice with DMF, twice with MeOH, twice with DCM and finally twice with THF. Resin was used immediately for step II.

Step II

Fmoc-Trp(Boc)-OH (161.4 mg, 526.6 g/mol, 0.31 mmol, 2 eq) was coupled to the resin using the same procedure and coupling agent as described in step II of example 18.

Step III

Possibly unreacted amino groups were acetylated using the procedure described in step III of example 18.

Step IV

Fmoc protection of the attached tryptophan was removed according to procedure described in step I but without any washes prior treatment with piperidine/DMF.

Step V

Fmoc-Lys(Boc)-OH (205.8 mg, 468.54 g/mol, 0.44 mmol, 3 eq) was coupled to resin bound compound using the same coupling agent and procedure as described in step II of example 18.

Step VI

Possibly unreacted amino groups were acetylated using the procedure described in step III.

Step VII

Fmoc protection of the attached lysine was removed according to procedure described in step I but without any washes prior to treatment with piperidine/DMF.

Step VIII

Benzenesulfonyl chloride (76.3 mg, 176.6 g/mol, 0.43 mmol, 3 eq) was introduced according to the procedure described in step VIII of example 18.

Step IX

Resin bound product was cleaved and Boc protection removed by treating the resin with 20 vol-% TFA in DCM (2.5 ml) for 45 minutes. Resulting red solution was collected and evaporated. Residue was purified with RP-HPLC to give 17.2 mg of 6-amino-(S)-2-(N-benzenesulfonylamino)-N'-((S)-1-carbamoyl-2-(1H-indol-3-yl)ethyl)hexanamide as white solid; overall yield 25%.

MS-ESI$^+$ (m/z): 472

$^1$H NMR (500 MHz, CD$_3$OD; δ, ppm): 7.74-7.72 (m, 2H), 7.61-7.59 (m, 1H), 7.49-7.46 (m, 1H), 7.37-7.34 (m, 3H), 7.14-7.10 (m, 2H), 7.06-7.03 (m, 1H), 4.45-4.43 (m, 1H), 3.67-3.64 (m, 1H), 3.35 (s, 2H), 3.24-3.20 (m, 1H), 3.02-2.97 (m, 1H), 2.74-2.70 (m, 2H), 1.54-1.42 (m, 4H), 1.21-1.09 (m, 2H).

Example 21

Synthesis of 5-amino-(S)-2-(N-benzenesulfonylamino)-N'-((S)-1-carbamoyl-2-phenylethyl)pentanamide Step I Rink amide resin (219.3 mg, 0.7 mmol/g, 0.15 mmol) was washed twice with DMF prior use. Washed resin was dissolved in 2.5 ml of 20 vol-% piperidine in DMF and mixture was agitated for 30 minutes. Resin was then washed thrice with DMF, twice with MeOH, twice with DCM and finally twice with THF. Resin was used immediately for step II.

Step II

Fmoc-Phe-OH (119.3 mg, 387.44 g/mol, 0.30 mmol, 2 eq) was coupled to the resin using the same procedure and coupling agent as described in step II of example 18.

Step III

Possibly unreacted amino groups were acetylated using the procedure described in step III in example 18.

Step IV

Fmoc protection of the attached phenylalanine was removed according to procedure described in step I but without any washes prior treatment with piperidine/DMF.

Step V

Fmoc-Orn(Boc)-OH (140.2 mg, 454.5 g/mol, 0.31 mmol, 2 eq) was coupled to resin bound compound using the same coupling agent and procedure as described in step II of example 18.

Step VI

Possibly unreacted amino groups were acetylated using the procedure described in step III.

Step VII

Fmoc protection of the attached ornithine was removed according to procedure described in step I but without any washes prior to treatment with piperidine/DMF.

Step VIII

Benzenesulfonyl chloride (81.3 mg, 176.62 g/mol, 0.46 mmol, 3 eq) was introduced according to the procedure described in step VIII of example 18.

Step IX

Resin bound product was cleaved and Boc protection removed by treating the resin with 20 vol-% TFA in DCM (2.5 ml) for 45 minutes. Resulting red solution was collected and evaporated. Residue was purified with RP-HPLC to give 16.1 mg of 5-amino-(S)-2-(N-benzenesulfonylamino)-N'-((S)-1-carbamoyl-2-phenylethyl)pentanamide as white solid, overall yield 25%.

MS-ESI$^+$ (m/z): 419

$^1$H NMR (500 MHz, CD$_3$OD; δ, ppm): 7.77 (m, 2H), 7.58 (m, 1H), 7.47-7.44 (m, 2H), 7.30-7.18 (m, 5H), 4.31 (m, 1H), 3.76 (m, 1H), 2.98 1H), 2.81-2.48 (m, 2H), 2.75 (m, 1H), 1.66-1.51 (m, 4H).

Example 22

Synthesis of 6-amino-N-((S)-1-carbamoyl-2-(1-naphthyl)ethyl)-(S)-2-(N'-(1-naphthalenesulfonyl)amino)hexanamide Step I Rink amide resin (218.3 mg, 0.7 mmol/g, 0.15 mmol) was washed twice with DMF prior use. Washed resin was dissolved in 2.5 ml of 20 vol-% piperidine in DMF and mixture was agitated for 30 minutes. Resin was then washed thrice with DMF, twice with MeOH, twice with DCM and finally twice with THF. Resin was used immediately for step II.

Step II

Fmoc-1-Naphthylalanine (134.4 mg, 437.49 g/mol, 0.31 mmol, 2 eq, PepTech) was coupled to the resin using the same procedure and coupling agent as described in step II of example 18.

Step III

Possibly unreacted amino groups were acetylated using the procedure described in step III in example 18.

Step IV

Fmoc protection of the attached naphthylalanine was removed according to procedure described in step I but without any washes prior treatment with piperidine/DMF.

Step V

Fmoc-Lys(Boc)-OH (218.0 mg, 468.54 g/mol, 0.46 mmol, 3 eq) was coupled to resin bound compound using the same coupling agent and procedure as described in step II of example 18.

Step VI

Possibly unreacted amino groups were acetylated using the procedure described in step III.

Step VII

Fmoc protection of the attached lysine was removed according to procedure described in step I but without any washes prior treatment with piperidine/DMF.

Step VIII

1-Naphthalenesulfonyl chloride (107.9 mg, 226.68 g/mol, 0.48 mmol, 3 eq) was introduced according to the procedure described in step VIII of example 18.

Step IX

Resin bound product was cleaved and Boc protection removed by treating the resin with 20 vol-% TFA in DCM (2.5 ml) for 45 minutes. Resulting red solution was collected and evaporated. The product was purified with RP-HPLC to give 10.5 mg of 6-amino-N-((S)-1-carbamoyl-2-(1-naphthyl)ethyl)-(S)-2-(N'-(1-naphthalenesulfonyl)amino)hexanamide as white solid; overall yield 25%.

MS-ESI$^+$ (m/z): 533

$^1$H NMR (500 MHz, CD$_3$OD; δ, ppm): 8.71 (d, 1H), 8.17 (m, 1H), 8.09 (d, 1H), 8.00-7.95 (m, 2H), 7.85 (m 1H), 7.75-7.69 (m, 2H), 7.62-7.59 (m, 1H), 7.55-7.47 (m, 3H), 7.36-7.33 (m, 1H), 7.30-7.28 (m, 1H), 4.49 (m, 1H), 3.56 (m, 1H), 3.41 (m, 1H), 3.01 (m, 1H), 2.56-2.52 (m, 2H), 1.39-1.21 (m, 4H), 1.04 (m, 1H), 0.87 (m, 1H).

Example 23

Synthesis of 6-amino-N-((S)-1-carbamoyl-2-(1H-indol-3-yl)ethyl)-(S)-2-(N'(1-naphthalenesulfonyl)amino)hexanamide Step I Rink amide resin (201.0 mg, 0.7 mmol/g, 0.14 mmol) was washed twice with DMF prior use. Washed resin was dissolved in 2.5 ml of 20 vol-% piperidine in DMF and mixture was agitated for 30 minutes. Resin was then washed thrice with DMF, twice with MeOH, twice with DCM and finally twice with THF. Resin was used immediately for step II.

Step II

Fmoc-Trp(Boc)-OH (147.2 mg, 526.6 g/mol, 0.28 mmol, 2 eq) was coupled to the resin using the same procedure and coupling agent as described in step II of example 18.

Step III

Possibly unreacted amino groups were acetylated using the procedure described in step III in example 18.

Step IV

Fmoc protection of the attached tryptophan was removed according to procedure described in step I but without any washes prior treatment with piperidine/DMF.

Step V

Fmoc-Lys(Boc)-OH (199.7 mg, 468.54 g/mol, 0.43 mmol, 3 eq) was coupled to resin bound compound using the same coupling agent and procedure as described in step II of example 18.

Step VI

Possibly unreacted amino groups were acetylated using the procedure described in step III.

Step VII

Fmoc protection of the attached lysine was removed according to procedure described in step I but without any washes prior treatment with piperidine/DMF.

Step VIII

1-Naphthalenesulfonyl chloride (97.9 mg, 226.68 g/mol, 0.43 mmol, 3 eq, Acros) was introduced according to the procedure described in step VIII of example 18.

Step IX

Resin bound product was cleaved and Boc protection removed by treating the resin with 20 vol-% TFA in DCM (2.5 ml) for 45 minutes. Resulting red solution was collected and evaporated. The product was purified with RP-HPLC to give 7.3 mg of 6-amino-N-((S)-1-carbamoyl-2-(1H-indol-3-yl)ethyl)(S)-2-(N'-(1-naphthalenesulfonyl)amino)hexanamide as white solid; overall yield 10%.

MS-ESI$^+$ (m/z): 522

$^1$H NMR (500 MHz, CD$_3$OD; δ, ppm): 8.68 (d, 1H), 8.14 (m, 1H), 8.06 (m, 1H), 7.96 (m, 1H), 7.69-7.59 (m, 2H), 7.52-7.34 (m, 3H), 7.12-7.00 (m, 3H), 4.36 (m, 1H), 3.60 (m, 1H), 3.12 (m, 1H), 2.86 (m, 1H), 2.55-2.51 (m, 2H), 1.49-1.23 (m, 4H), 1.11-0.90 (m, 2H).

Example 24

Synthesis of 6-amino-(S)-2-(N-(4-butoxy-1-benzenesulfonyl)amino)-N'-((S)-1-carbamoyl-2-phenylethyl)hexanamide Step I Rink amide resin (195.3 mg, 0.7 mmol/g, 0.14 mmol) was washed twice with DMF prior use. Washed resin was dissolved in 2.5 ml of 20 vol-% piperidine in DMF and mixture was agitated for 30 minutes. Resin was then washed thrice with DMF, twice with MeOH, twice with DCM and finally twice with THF. Resin was used immediately for step II.

Step II

Fmoc-Phe-OH (105.3 mg, 387.4 g/mol, 0.27 mmol, 2 eq) was coupled to the resin using the same procedure and coupling agent as described in step II of example 18.

Step III

Possibly unreacted amino groups were acetylated using the procedure described in step III of example 18.

Step IV

Fmoc protection of the attached phenylalanine was removed according to procedure described in step I but without any washes prior treatment with piperidine/DMF.

Step V

Fmoc-Lys(Boc)-OH (196.1 mg, 468.54 g/mol, 0.42 mmol, 3 eq) was coupled to resin bound compound using the same coupling agent and procedure as described in step II of example 18.

Step VI

Possibly unreacted amino groups were acetylated using the procedure described in step III.

Step VII

Fmoc protection of the attached lysine was removed according to procedure described in step I but without any washes prior treatment with piperidine/DMF.

Step VIII 4-(n-Butoxy)benzenesulfonyl chloride (106.6 mg, 248.73 g/mol, 0.43 mmol, 3 eq) was introduced according to the procedure described in step VIII of example 18.

Step IX

Resin bound product was cleaved and Boc protection removed by treating the resin with 20 vol-% TFA in DCM (2.5 ml) for 45 minutes. Resulting red solution was collected and evaporated. The product was purified with RP-HPLC to give 18.3 mg of 6-amino-(S)-2-(N-(4-butoxy-1-benzenesulfonyl)amino)-N'-((S)-1-carbamoyl-2-phenylethyl)hexanamide as white solid, overall yield 35%.

MS-ESI$^+$ (m/z): 505

$^1$H NMR (500 MHz, CD$_3$OD; δ, ppm): 7.71 (m, 2H), 7.29-7.19 (m, 5H), 6.98 (m, 2H), 4.41 (m, 1H), 4.00 (m, 2H), 3.62 (m, 1H), 3.05 (m, 1H), 2.82-2.73 (m, 3H), 1.77-1.71 (m, 2H), 1.57-1.43 (m, 6H), 1.31-1.09 (m, 2H), 0.98-0.95 (m 3H).

Example 25

Synthesis of N-((S)-1-carbamoyl-2,2-diphenylethyl)-5-guanidino-(S)-2-(N'-(4-methyl-1-naphthalene-sulfonyl)amino)pentanamide (Compound 6)

Step I

Rink amide resin (1.5 g, 0.7 mmol/g, 1.02 mmol) was washed twice with DMF prior use. Washed resin was dissolved in 21 ml of 20 vol-% piperidine in DMF and mixture was agitated for 50 minutes. Resin was then washed thrice with DMF, thrice with MeOH, twice with DCM and finally twice with THF. Resin was used immediately for step II.

Step II

Fmoc-L-3,3-diphenylalanine (1.41 g, 463.53 g/mol, 3.05 mmol, 3 eq, PepTech) and DIC (477.3 µl, 126.20 g/mol, 0.806 g/cm$^3$, 3.05 mmol, 3 eq) were dissolved in dry DMF (21 ml) and after 10 minutes mixed with the resin. After 22 hours agitation, solvent was filtered out and fresh solution with similar amounts of Fmoc-L-3,3-diphenylalanine and DIC in dry DMF was introduced. After additional 5 hours, solvent was again filtered out and resin washed thrice with DMF, thrice with MeOH, thrice with DCM and thrice with THF.

Step III

Possibly unreacted amino groups of the resin were acetylated with a solution consisting of acetic anhydride (700 µl, 102.09 g/mol, 1.087 g/cm$^3$, 7.5 mmol) and DIPEA (119 µl, 129.25 g/mol, 0.755 g/cm$^3$, 0.7 mmol) in dry DMF (16.1 ml) for 45 minutes. Resin was then filtered and washed thrice with DMF, thrice with MeOH, twice with DCM and twice with THF.

Step IV

Fmoc protection of the attached 3,3-diphenylalanine was removed according to procedure described in step I but without any washes prior treatment with piperidine/DMF.

Step V

Fmoc-Arg(Pmc)-OH (1.34 g, 662.8 g/mol, 2.03 mmol, 2 eq) was coupled to resin bound compound using the same coupling agent and procedure as described in step II.

Step VI

Possibly unreacted amino groups of 3,3-diphenylalanine were acetylated using the procedure described in step III.

Step VII

Fmoc protection of the arginine attached in step V was removed according to procedure described in step I but again without any washes prior treatment with piperidine/DMF.

Step VIII

4-Methyl-1-naphthalenesulfonyl chloride (733.7 mg, 240.71 g/mol, 3.0 mmol, 3 eq, Maybridge) was dissolved in dry THF (21 ml) and mixed with the resin. TEA (422.5 µl, 101.19 g/mol, 0.73 g/cm$^3$, 3.0 mmol, 3 eq, Baker) was then added to the mixture. After overnight agitation, solvent was filtered and resin washed thrice with THF, thrice with MeOH, thrice with DMF, once with MeOH and finally thrice with DCM.

Step IX

Resin bound product was cleaved and Pmc protection removed by treating the resin with 50 vol-% TFA in DCM (21 ml) for 1 hour. Resulting red solution was collected and evaporated. Product was purified with RP-HPLC to give 108.4 mg of N-((S)-1-carbamoyl-2,2-diphenylethyl)-5-guanidino-(S)-2-(N'-(4-methyl-1-naphthalenesulfonyl) amino)pentanamide as white solid, overall yield 16.4%.

MS-ESI$^+$ (m/z): 601

$^1$H NMR (500 MHz, CD$_3$OD; δ, ppm): 8.71 (m, 1H), 8.17 (m, 1H), 7.94 (m, 1H), 7.69-7.65 (m, 2H), 7.35 (m, 1H), 7.27-7.19 (m, 9H), 7.17-7.13 (m, 2H), 5.11 (m, 1H), 4.38 (d, 1H), 3.46 (m, 1H), 2.77 (s, 3H), 2.76-2.65 (m, 2H), 1.44-1.02 (m, 4H).

Example 26

Synthesis of 4-amino-N-((S)-1-carbamoyl-2-phenyl-ethyl)-(S)-2-(N'-methyl-N'-(4-methyl-1-naphthalene-sulfonyl)amino)butanamide Step I Rink amide resin (223.6 mg, 0.7 mmol/g, 0.16 mmol) was washed twice with dry DMF prior use. Washed resin was dissolved in 2.5 ml of 20 vol-% piperidine in DMF and mixture was agitated for 30 minutes. Resin was then washed thrice with DMF, twice with MeOH, twice with DCM and finally twice with THF. Resin was used immediately for step II.

Step II

Fmoc-Phe-OH (184 mg, 387.44 g/mol, 0.47 mmol, 3 eq) and DIC (74 µl, 126.20 g/mol, 0.806 g/cm$^3$, 0.47 mmol, 3 eq) were dissolved in dry DMF and after 5 minutes mixed with the resin. After 6 hours agitation, solvent was filtered out and fresh solution with same amounts of Fmoc-Phe-OH and DIC in dry DMF was introduced. After additional 6 hours solvent was again filtered out and resin washed twice with DMF, twice with MeOH, once with DCM and once with THF.

Step III

Possibly unreacted amino groups were acetylated by treating the resin with acetic anhydride (100 µl, 102.09 g/mol, 1.087 g/cm$^3$, 1.06 mmol), DIPEA (17 µl, 129.25 g/mol, 0.755 g/cm$^3$, 0.1 mmol) and dry DMF (2.1 ml) for 30 minutes. Resin was then filtered and washed twice with DMF, twice with MeOH, once with DCM and once with THF.

Step IV

Fmoc protection of the phenylalanine was removed according to procedure described in step I but without any washes prior treatment with piperidine/DMF.

Step V

Fmoc-Dbu(Boc)-OH (211.3 mg, 440.5 g/mol, 0.47 mmol, 3 eq) was coupled to resin bound compound using same coupling agents and procedure as described in step II.

Step VI

Possibly unreacted amino groups were acetylated using the procedure described in step III.

Step VII

Fmoc protection of the amino acid attached in step V was removed according to procedure described in step I but without any washes prior treatment with piperidine/DMF.

Step VIII

4-Methyl-1-naphthalenesulfonyl chloride (115 mg, 240.71 g/mol, 0.47 mmol, 3 eq, Maybridge) was dissolved in dry THF (2.5 ml), mixed with the resin and TEA (65 µl, 101.19 g/mol, 0.73 g/cm$^3$, 0.47 mmol, 3 eq, Baker) was added to the mixture. After overnight agitation, solvent was filtered and resin washed thrice with THF, twice with MeOH, twice with DMF, once with MeOH and finally thrice with DCM.

Step IX

Resin (0.16 mmol) was swollen with dry DMF (2.5 ml) and DBU (240 µl, 152.24 g/mol, 1.018 g/cm$^3$, 1.6 mmol, 10 eq, Acros) was added to the mixture. Methyl iodide (1.6 mmol, 141.94 g/mol, 2.28 g/cm$^3$, 1.6 mmol, 10 eq, Acros) was then added dropwise to the mixture. After overnight agitation solvent was filtered and resin washed twice with DMF, twice with MeOH, twice with DCM and twice with THF.

Step X

Resin bound product was cleaved and Boc protection removed by treating the resin with 25 vol-% TFA in DCM (2.5 ml) for 45 minutes. Resulting red solution was collected and evaporated. Residue was purified with RP-HPLC to give 10.2 mg of 4-amino-N-((S)-1-carbamoyl-2-phenylethyl)-(S)-2-(N'-methyl-N'-(4-methyl-1-naphthalenesulfonyl)amino)butanamide as white solid, overall yield 13%.

MS-ESI$^+$ (m/z): 483

$^1$H NMR (500 MHz, CD$_3$OD; δ, ppm): 8.64 (m, 1H), 8.28 (m, 1H), 8.16 (d, 1H), 7.75 (m, 2H), 7.52 (d, 1H), 7.05 (m, 1H), 6.98 (t, 2H), 6.69 (d, 2H), 4.78 (m, 1H, shielded), 4.42 (m, 1H), 3.00 (m, 1H), 2.82 (s, 3H), 2.79 (t, 2H), 2.34 (m, 1H), 2.23 (s, 3H), 2.12 (m, 1H), 1.75 (m, 1H).

Example 27

Synthesis of 4-amino-N-((S)-1-hydroxymethyl-2-phenylethyl)-(S)-2-(N'-4-methyl-1-naphthalenesulfonylamino)butanamide

Step I

Trityl resin (129.0 mg, 1.5 mmol/g, 0.19 mmol) was washed twice with dry DMF prior use. Fmoc-phenylaninol (220.8 mg, 373.45 g/mol, 0.58 mmol, 3 eq, Advanced ChemTech) and DIPEA (106 µl, 129.25 g/mol, 0.755 g/cm$^3$, 0.58 mmol, 3 eq) were dissolved in dry DMF and after 5 minutes mixed with the resin. After 4 hours, solvent was filtered out and fresh solution with same amounts of Fmoc-phenylaninol and DIPEA in dry DMF was introduced. After overnight agitation solvent was again filtered out and resin washed twice with DMF, twice with MeOH, once with DCM and once with THF.

Step II

Possibly unreacted chloro groups were capped by treating the resin with methanol (300 µl, 32.04 g/mol, 0.79 g/cm$^3$, 7.4 mmol) and DIPEA (100 µl, 129.25 g/mol, 0.755 g/cm$^3$, 0.1 mmol) in dry DCM (1.7 ml) for 30 minutes. Resin was then filtered and washed twice with DCM, twice with MeOH, once with DMF and once with THF.

Step III

Dissolving the resin in 2.5 ml of 20 vol-% piperidine in DMF and agitating the mixture for 30 minutes removed the Fmoc protection. Resin was then washed thrice with DMF, twice with MeOH, twice with DCM and finally twice with THF. Resin was used immediately for step IV.

Step IV

Fmoc-Dbu(Boc)-OH (254.7 mg, 440.48 g/mol, 0.57 mmol, 3 eq) was coupled to resin bound compound using same coupling agent and procedure as described in step II of example 26.

Step V

Possibly unreacted amino groups were acetylated by treating the resin with acetic anhydride (100 µl, 102.09 g/mol, 1.087 g/cm$^3$, 1.06 mmol) and DIPEA (17 µl, 129.25 g/mol, 0.755 g/cm$^3$, 0.1 mmol) in dry DMF (2.1 ml) for 30 minutes. Resin was then filtered and washed twice with DMF, twice with MeOH, once with DCM and once with THF.

Step VI

Fmoc protection of the amino acid attached in step IV was removed according to procedure described in step III.

Step VII

4-Methyl-1-naphthalenesulfonyl chloride (115.4 mg, 240.71 g/mol, 0.47 mmol, 3 eq, Maybridge) dissolved in dry THF (2.5 ml) was mixed with the resin and TEA (65 µl, 101.19 g/mol, 0.73 g/cm$^3$, 0.47 mmol, 3 eq, Baker) was added to the mixture. After overnight agitation, solvent was filtered and resin washed thrice with THF, twice with MeOH, twice with DMF, once with MeOH and finally thrice with DCM.

Step VIII

Resin bound product was cleaved and Boc protection removed by treating the resin with 5 vol-% TFA in DCM (2.5 ml) for 45 minutes. Resulting red solution was collected and evaporated. 14 mg of 4-amino-N-((S)-1-hydroxymethyl-2-phenylethyl)-(S)-2-(N'-4-methyl-1-naphthalenesulfonylamino)butanamide as a yellow oil was obtained. The product was further purified with RP-HPLC to give 2.3 mg of 4-amino-N-((S)-1-hydroxymethyl-2-phenylethyl)(S)-2-(N'-4-methyl-1-naphthalenesulfonylamino)butanamide as white solid, overall yield 3%.

MS-ESI$^+$ (m/z): 456

$^1$H NMR (500 MHz, CD$_3$OD; δ, ppm): 8.70 (d, 1H), 8.13 (d, 1H), 8.11 (d, 1H), 7.73-7.63 (m, 2H), 7.42 (d, 1H), 7.20-7.10 (m, 3H), 6.95 (d, 2H), 3.83 (m, 1H), 3.63 (m, 1H), 3.16 (m, 1H), 3.05 (m, 1H), 2.94-2.81 (m, 2H), 2.70 (s, 3H), 2.29 (m, 1H), 2.00-1.89 (m, 2H), 1.81 (m, 1H).

Example 28

Additional compounds (including but not restricted to those described below) were prepared according to methods described in examples 1-27 but using the corresponding starting materials.

| Name | MS-ESI$^+$ (m/z) | Example |
|---|---|---|
| 5-amino-N-((S)-1-carbamoyl-2-phenylethyl)-(S)-2-(N'-(4-methyl-1-naphthalenesulfonyl)amino)pentanamide (Compound 7) | 483 | 18 |
| 4-amino-N-((S)-1-carbamoyl-2-phenylethyl)-(S)-2-(N'-(4-ethyl-1-naphthalenesulfonyl)amino)butanamide (Compound 8) | 483 | 18 |
| 4-amino-N-((S)-1-carbamoyl-2,2-diphenylethyl)-(S)-2-(N'-(4-methyl-1-naphthalenesulfonyl)amino)butanamide (Compound 9) | 545 | 18 |
| 4-amino-N-((S)-1-carbamoyl-2-phenylethyl)-(S)-2-(N'-(1-naphthalenesulfonyl)amino)butanamide (Compound 10) | 455 | 18 |
| N-benzyl-4-N'-cyclohexylamino-(S)-2-(N''-(4-methyl-1-naphthalenesulfonyl)amino)butanamide (Compound 11) | 494 | 1, 14 |
| (S)-2-N-(4-butoxybenzenesulfonyl)amino-N'-((S)-1-carbamoyl-2-phenylethyl)-5-guanidinopentanamide (Compound 12) | 533 | 17 |
| 4-amino-N-((S)-1-carbamoyl-2-methylpropyl)-(S)-2-(N'-(4-methyl-1-naphthalenesulfonyl)amino)butanamide (Compound 13) | 421 | 18 |
| 4-amino-(S)-2-N-(4-bromo-2-ethylbenzenesulfonyl)-amino-N'-((S)-1-carbamoyl-2-phenylethyl)butanamide (Compound 14) | 511, 513 | 18 |

-continued

| Name | MS-ESI⁺ (m/z) | Example |
|---|---|---|
| N-1-carbamoyl-2-phenylethyl-(S)-2-N'-(4-chloro-3-nitrobenzenesulfonyl)amino-5-guanidinopentanamide | 540 | 17 |
| N-(1-carbamoyl-2-phenylethyl)-5-guanidino-(S)-2-(N'-(2,4,6-triisopropyl-benzenesulfonyl)amino)pentanamide | 587 | 17 |
| N-((S)-1-carbamoyl-2-phenylethyl)-5-guanidino-(S)-2-(N'-(2-naphthalene-sulfonyl)amino)pentanamide (Compound 15) | 511 | 17 |
| N-((S)-1-carbamoyl-2-phenylethyl)-5-guanidino-(S)-2-(N'-(3-phenylben-zenesulfonyl)amino)pentanamide (Compound 16) | 537 | 17 |
| 5-N-isopropylamino-(S)-2-N'-(4-methyl-1-naphthalene-sulfonyl)amino-N''-(1,2,3,4-tetrahydro-1-naphthyl)-pentanamide (Compound 17) | 508 | 1, 14 |
| N-((S)-1-carbamoyl-2-phenylethyl)-6-guanidino-(S)-3-(N'-(4-methyl-1-naphthalenesulfonyl)amino)hexanamide | 539 | 17 |
| 4-amino-(S)-2-N-(4-methyl-1-naphtha-lenesulfonyl)-amino-N'-(1,2,3,4-tetrahydro-1-naphthyl)butanamide (Compound 18) | 452 | 1 |
| N-((S)-1-carbamoyl-2-phenylethyl)-5-guanidino-(S)-2-(N'-(4-phenylben-zenesulfonyl)amino)pentanamide | 537 | 17 |
| 5-amino-N-(2-(2-carbamoyl)indanyl)-(S)-2-(N'-(4-methyl-1-naphthalene-sulfonyl)amino)pentanamide (Compound 19) | 495 | 18 |
| 5-amino-N-(2-(1H-indol-3-yl)ethyl)-(S)-2-(N'-(4-methyl-1-naphthalene-sulfonyl)amino)pentanamide (Compound 20) | 479 | 1 |
| 5-amino-N-((S)-1-carbamoyl-2-phenyl-ethyl)-(S)-2-(N'-(2-phenylbenzene-sulfonyl)amino)pentanamide | 495 | 18 |
| 5-amino-N-((S)-1-carbamoyl-2-(3-chloro-phenyl)ethyl)-(S)-2-(N'-(4-methyl-1-naphthalenesulfonyl)amino)-pent-anamide (Compound 21) | 517 | 18 |
| 5-amino-N-(2-(2-carbamoyl)-1,2,3,4-te-trahydronaphthyl)-(S)-2-(N'-(4-methyl-1-naphthalenesulfonyl)amino)-pentanamide (Compound 22) | 509 | 18 |
| N-(2-(3-chlorophenyl)ethyl)-4-N'-methylamino-(S)-2-(N''-(4-methyl-1-naphthalenesulfonyl)amino)-butanamide (Compound 23) | 474 | 1, 14 |
| N-((S)-1-carbamoyl-2-phenylethyl)-5-guanidino-(S)-2-(N'-(8-quinoline-sulfonyl)amino)pentanamide | 512 | 17 |
| (S)-2-N-(4-acetylbenzenesulfonyl)amino-N'-((S)-1-carbamoyl-2-phenylethyl)-5-guanidinopentanamide | 503 | 17 |
| N-benzyl-5-N',N'-dimethylamino-(S)-2-(N''-(4-methyl-1-naphthalene-sulfonyl)amino)pentanamide | 454 | 1, 14 |
| 5-amino-N-((S)-1-carbamoyl-2-phenyleth-yl)-(S)-2-(N'-(3-thiophenesulfo-nyl)amino)pentanamide | 425 | 18 |
| 5-amino-(S)-2-N-(3-benzo[b]thio-phenesulfonyl)amino-N'-((S)-1-car-bamoyl-2-phenylethyl)pentanamide | 475 | 18 |
| 5-amino-N-((S)-1-carbamoyl-2-phenyleth-yl)-(S)-2-(N'-(5-(1,3-oxazol-5-yl)-2-thiophenesulfonyl)amino)-pentanamide | 492 | 18 |
| 5-amino-N-((S)-1-carbamoyl-2-phenyleth-yl)-(S)-2-(N'-(5-chloro-1-naphtha-lenesulfonyl)amino)pentanamide | 503 | 18 |
| N-((S)-1-carbamoyl-2-(4-biphenyl)ethyl)-5-guanidino(S)-2-(N'-(1-naphthalene-sulfonyl)amino)pentanamide | 587 | 17 |
| 5-amino-N-((S)-1-carbamoyl-2-(3-pyridin-yl)ethyl)-(S)-2-(N'-(4-methyl-1-naphthalenesulfonyl)amino)pentanamide | 484 | 18 |
| 5-amino-N-((S)-1-carbamoyl-2-phenyleth-yl)-N-methyl-(S)-2-(N'-(4-methyl-1-naphthalenesulfonyl)amino)-pentanamide | 497 | 18 |
| 5-amino-N-(2-benzyloxy-(S)-1-carbamoyl-ethyl)-(S)-2-(N'-(4-methyl-1-naph-thalenesulfonyl)amino)pentamide | 513 | 18 |
| 4-amino-(S)-2-N-(4-methyl-1-naphtha-lenesulfonyl)-amino-N'-1-naphthyl-butanamide | 448 | 1 |
| 4-amino-N-cyclohexyl-(S)-2-(N'-(4-methyl-1-naphthalene-sulfonyl)amino)bu-tanamide | 404 | 1 |
| 4-amino-(S)-2-(N-(4-methyl-1-naphtha-lenesulfonyl)-amino)butanamide | 322 | 18 |
| 5-amino-(S)-2-N-(4-methyl-1-naphtha-lenesulfonyl)-amino-N'-(1,2,3,4-tetrahydro-1-naphthyl)pentanamide | 466 | 1 |
| 5-N-methylamino-(S)-2-N'-(4-methyl-1-naphthalene-sulfonyl)amino-N''-(1,2,3,4-tetrahydro-1-naph-thyl)-pentanamide | 480 | 1, 14 |

Example 29

Binding Affinity at the Human Somatostatin Receptor Subtypes

The affinity of the compounds of the invention for the five human somatostatin receptor subtypes (SSTR1, SSTR2, SSTR3, SSTR4, and SSTR5) was determined in competition binding assays with ($^{125}$I-Tyr)-[Leu$^8$,DTrp$^{22}$]-somatostatin-28 ($^{125}$I-LTT-sst-28). The biological material for these experiments consisted of membranes from Chinese hamster ovary (CHO) cells stably transfected with one of the five human somatostatin receptor subtypes. Membranes (3-20 µg of total protein per sample) and trace amount of $^{125}$I-LTT-sst-28 were incubated in 10 mM Hepes, 1 mM EDTA, 5 mM MgCl$_2$, 5 mg/ml of BSA and 30 µg/ml bacitracin, pH 7.6 with six concentrations of the compounds. Each concentration was run in duplicate. Nonspecific binding was defined by 1 µM somatostatin-14 (sst-14) and corresponded to 5-25% of total binding. After 60 min at room temperature, incubations were terminated by rapid vacuum filtration through GF/B glass fiber filter mats (presoaked at 4° C. in 200 ml of 10 mM Hepes, 1 mM EDTA, 5 mM MgCl$_2$, pH 7.6) and three 5 ml washes with ice-cold wash buffer (20 mM TRIS, 1 mM EDTA, 5 mM MgCl$_2$, pH 7.4). The filters were then dried, impregnated with scintillate and their radioactivity was measured by scintillation counting. The analysis of the experiments was carried out by nonlinear least square curve fitting. Affinity constants ($K_i$) were calculated from the IC$_{50}$ values according to the Cheng-Prusoff's equation (Cheng and Prusoff, 1973). Experiments were repeated a minimum of three times.

Using the aforementioned protocol, the following test results were obtained.

| Compound | $K_i$(SSTR1)/nM | $K_i$(SSTR2)/nM | $K_i$(SSTR3)/nM | $K_i$(SSTR4)/nM | $K_i$(SSTR5)/nM |
|---|---|---|---|---|---|
| Compound 17 | 1.0 ± 0.4 | >10 000 | >2 000 | 84 ± 23 | >10 000 |
| Compound 2 | 500 ± 150 | >5 000 | 1 400 ± 100 | 1.2 ± 0.4 | 540 ± 80 |

Besides these, a large set of compounds had $K_i$ less than 300 nM for SSTR1. Among this set were for example:
Compound 3
Compound 5
Compound 6
Compound 7
Compound 11
Compound 12
Compound 15
Compound 18
Compound 21
Compound 22
Compound 23

Furthermore, another subset of the compounds of the invention had $K_i$ less than 300 nM for SSTR4. Among this set were for example:
Compound 1
Compound 3
Compound 4
Compound 5
Compound 6
Compound 7
Compound 8
Compound 9
Compound 10
Compound 13
Compound 14
Compound 16
Compound 19
Compound 20

REFERENCES

Aavik et al. (2002), *Elimination of vascular fibrointimal hyperplasia by somatostatin receptor 1,4-selective agonist*. FASEB J 16:724-6

Bito et al. (1994), *Functional coupling of SSTR4, a major hippocampal somatostatin receptor, to adenylate cyclase inhibition, arachidonate release, and activation of the mitogen-activated protein kinase cascade*. J Biol Chem 269:12722-12730

Bonini et al. (2000), *Identification and characterization of two G protein-coupled receptors for NPFF*. J Biol. Chem. 275: 39324-39331

Bourguignon et al. (1997), *Analogs of NPFF, a neuropeptide which modulates morphine analgesia*. Proceedings of the XIVth International Symposium on Medicinal Chemistry, Awouters F (ed.), Elsevier Science B. V., pp. 35-44

Brussaard et al. (1989), *Peripheral injection of DNS-RFa, a FMRFa agonist, suppresses morphine-induced analgesia in rats*. Peptides 10:735-739

Cheng and Prusoff (1973), *Relationship between the inhibition constant (KI) and the concentration of inhibitor which causes 50 percent inhibition (I50) of an enzymatic reaction*, Biochem. Pharmacol. 22:3099-3108

Curtis et al. (2000), *Somatostatin receptor subtype expression and function in human vascular tissue*. Am J Physiol Heart Circ Physiol 278:H1815-1822

Eriksen et al. (1995), *Randomized double-blind Scandinavian trial of angiopeptin versus placebo for the prevention of clinical events and restenosis after coronary balloon angioplasty*. Am Heart J 130:1-8

Gicquel et al. (1994), *Structure-activity study of neuropeptide FF: contribution of N-terminal regions to affinity and activity*. J Med. Chem. 37:3477-3481

Hoyer et al. (1995), *Classification and nomenclature of somatostatin receptors*. TIPS 16:86-88

Mazarguil et al. (2001), *Structure-activity relationships of neuropeptide FF: role of C-terminal regions*. Peptides 22:1471-1478

Mori et al. (1997), *Differential expression of somatostatin receptors in the rat eye: SSTR4 is intensely expressed in the iris/ciliary body*. Neurosci Left 223:185-188

Patel (1999), *Somatostatin and its receptor family*. Front Neuroendocrinol 20:157-198

Payza et al. (1993), *Neuropeptide FF receptors: structure-activity relationship and effect of morphine*. J Pharmacol Exp Ther 267:88-94

Reisine and Bell (1995), *Molecular biology of somatostatin receptors*. Endocrine Reviews 16:427-442

Reubi et al. (1998), *A selective analog for the somatostatin sst1-receptor subtype expressed by human tumors*. Eur J Pharmacol 345:103-110

Reubi et al. (2001), *Somatostatin receptor sst1-sst5 expression in normal and neoplastic human tissues using receptor autoradiography with subtype-selective ligands*. Eur J Nucl Med 28:836-846

Rivier et al. (2001), *Potent somatostatin undecapeptide agonists selective for somatostatin receptor 1 (sst1)*. J Med Chem 44:2238-2246

Rohrer et al. (1998), *Rapid identification of subtype-selective agonists of the somatostatin receptor through combinatorial chemistry*. Science 282:737-740

Sinisi et al. (1997), Different expression patterns of somatostatin receptor subtypes in cultured epithelial cells from human normal prostate and prostate cancer. J Clin Endocrinol Metab 82:2566-2569 von Essen et al. (1997), *Effects of octreotide treatment on restenosis after coronary angioplasty: results of the VERAS study*. Circulation 96:1482-1487

Yang et al. (1985), *Isolation, sequencing, synthesis, and pharmacological characterization of two brain neuropeptides that modulate the action of morphine*. Proc Natl Acad Sci 82:7757-7761

The invention claimed is:
1. A compound of Formula II

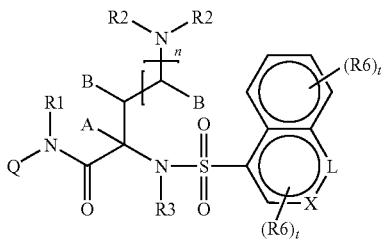

(II)

or a pharmaceutically acceptable salt or ester thereof, wherein
Q is
1) H,
2) aryl or
3) heteroaryl, wherein aryl and heteroaryl are unsubstituted or substituted with 1 to 4 substituents selected from $R^a$, or
4) a group of formula

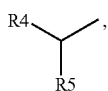

wherein R4 is
1) H,
2) $(C_1-C_6)$alkyl,
3) $(C_2-C_6)$alkenyl,
4) $(C_2-C_6)$alkynyl,
5) Cy,
6) Cy-$(C_1-C_6)$alkyl,
7) Cy-$(C_2-C_6)$alkenyl or
8) Cy-$(C_2-C_6)$alkynyl, wherein alkyl, alkenyl, alkynyl and Cy are unsubstituted or substituted with 1 or 2 substituents selected from $R^d$,
R5 is
1) H,
2) $(C_1-C_6)$alkyl,
3) $(C_2-C_6)$alkenyl,
4) $(C_2-C_6)$alkynyl,
5) aryl,
6) aryl-$(C_1-C_6)$alkyl,
7) heteroaryl or
8) heteroaryl-$(C_1-C_6)$alkyl, wherein aryl and heteroaryl are unsubstituted or substituted with 1 to 4 substituents selected from $R^d$, or
R4 and R5 together with the atom to which they are attached form a 3- to 8-membered ring containing 0 to 2 heteroatoms selected from the group consisting of N, O and S, wherein said ring is unsubstituted or substituted with 1 to 3 substituents selected from $R^d$, or said ring is fused to aryl or heteroaryl, either of which is unsubstituted or substituted with 1 to 3 substituents selected from $R^d$;
A is
1) H,
2) $(C_1-C_6)$alkyl or
3) $(C_3-C_5)$cycloalkyl;

B is independently
1) H,
2) halogen or
3) $(C_1-C_6)$alkyl, or
symbols B together form a double or triple bond between the atoms to which they are attached;
R1 is
1) H,
2) $(C_1-C_6)$alkyl or
3) $(C_3-C_7)$cycloalkyl;
R2 is independently
1) H,
2) $(C_1-C_6)$alkyl,
3) $(C_2-C_6)$alkenyl,
4) $(C_2-C_6)$alkynyl,
5) $(C_3-C_7)$cycloalkyl or
6) $(C_3-C_7)$cycloalkyl$(C_1-C_6)$alkyl, or
symbols R2 together with the nitrogen to which they are attached form a saturated 5- to 7-membered ring containing 1 or 2 heteroatoms selected from the group consisting of N, O and S;
R3 is
1) H,
2) $(C_1-C_6)$alkyl,
3) $(C_2-C_6)$alkenyl,
4) $(C_2-C_6)$alkynyl or
5) $(C_3-C_7)$cycloalkyl;
R6 is independently
1) H,
2) halogen,
3) —$NO_2$,
4) —$NR^bR^b$,
5) —CN,
6) —$OR^b$,
7) —$SR^b$,
8) —$C(O)R^b$,
9) $(C_1-C_6)$alkyl,
10) $(C_2-C_6)$alkenyl,
11) $(C_2-C_6)$alkynyl,
12) $(C_3-C_7)$cycloalkyl or
13) —$CF_3$;
$R^a$ is independently
1) H,
2) halogen,
3) —$OR^b$,
4) $(C_1-C_6)$alkyl or
5) —$CF_3$;
$R^b$ is independently
1) hydrogen,
2) $(C_1-C_6)$alkyl,
3) $(C_2-C_6)$alkenyl,
4) $(C_2-C_6)$alkynyl,
5) Cy or
6) Cy-$(C_1-C_4)$alkyl;
$R^d$ is independently
1) a group selected from $R^c$,
2) $(C_1-C_6)$alkyl,
3) $(C_2-C_6)$alkenyl,
4) $(C_2-C_6)$alkynyl,
5) aryl,
6) aryl-$(C_1-C_6)$alkyl,
7) heteroaryl-$(C_1-C_6)$alkyl,
8) $(C_3-C_7)$cycloalkyl or
9) heterocyclyl, wherein alkyl, alkenyl, alkynyl, aryl and heteroaryl are unsubstituted or substituted with 1 to 4 substituents independently selected from $R^c$;

$R^c$ is independently
1) a group selected from $R^a$,
2) —NO$_2$,
3) —SR$^b$,
4) —NR$^b$R$^b$,
5) —CN or
6) —NR$^b$C(O)R$^b$;

Cy is cycloalkyl, heterocyclyl, aryl or heteroaryl;
t is an integer from 0 to 3;
n is the integer 1 or 2;
X is a bond or C(R6); and
L is C(R6), S or N.

2. A compound according to claim 1, which is a compound of Formula IIA (IIA)

wherein R2, R3, B, n and t are defined as in claim 1;
R4 is phenyl or benzyl, either of which is unsubstituted or substituted with 1 or 2 substituents selected from $R^a$ as defined in claim 1;
R5 is H or (C$_1$-C$_6$)alkyl; and
R6 is independently selected from H, halogen or (C$_1$-C$_6$)alkyl.

3. A compound according to claim 1, which is a compound of Formula IIB (IIB)

wherein Q, R3, R6, n and t are defined as in claim 1; and
R2 is independently selected from H, methyl, ethyl, isopropyl, cyclopropyl or cyclohexyl.

4. A compound according to claim 1, wherein R3 is H or methyl.

5. A compound according to claim 1, wherein L is C(R6), X is a bond or C(R6) and R6 is H.

6. A compound according to claim 1, wherein L and X are each C(R6) and R6 is independently H, (C$_1$-C$_6$)alkyl or halogen.

7. A compound according to claim 1, wherein L is N or S and X is a bond.

8. A compound of Formula II according to claim 1, wherein the compound is 4-amino-(S)-2-N-(4-methyl-1-naphthalenesulfonyl)amino-N'-(1,2,3,4-tetrahydro-1-naphthyl)butanamide, 5-amino-(S)-2-N-(4-methyl-1-naphthalenesulfonyl)amino-N'-(1,2,3,4-tetrahydro-1-naphthyl)pentanamide, 4-amino-N-2-(3-chlorophenyl)ethyl-(S)-2-(N'-(4-methyl-1-naphthalenesulfonyl)amino)butanamide, 5-N-methylamino-(S)-2-N'-(4-methyl-1-naphthalenesulfonyl)amino-N''-(1,2,3,4-tetrahydro-1-naphthyl)pentanamide or N-benzyl-4-(N'-isopropyl)amino-(S)-2-(N''-(4-methyl-1-naphthalenesulfonyl)amino)butanamide.

9. A process for preparing a compound as claimed in claim 1, comprising reacting an amidated amino acid of Formula III (III)

wherein
Q is
1) H,
2) aryl or
3) heteroaryl, wherein aryl and heteroaryl are unsubstituted or substituted with 1 to 4 substituents selected from $R^a$, or
4) a group of formula wherein R4 is
1) H,
2) (C$_1$-C$_6$)alkyl,
3) (C$_2$-C$_6$)alkenyl,
4) (C$_2$-C$_6$)alkynyl,
5) Cy,
6) Cy-(C$_1$-C$_6$)alkyl,
7) Cy-(C$_2$-C$_6$)alkenyl or
8) Cy-(C$_2$-C$_6$)alkynyl, wherein alkyl, alkenyl, alkynyl and Cy are unsubstituted or substituted with 1 or 2 substituents selected from $R^d$, R5 is
1) H,
2) (C$_1$-C$_6$)alkyl,
3) (C$_2$-C$_6$)alkenyl,
4) (C$_2$-C$_6$)alkynyl,
5) aryl,
6) aryl-(C$_1$-C$_6$)alkyl,
7) heteroaryl or
8) heteroaryl-(C$_1$-C$_6$)alkyl, wherein aryl and heteroaryl are unsubstituted or substituted with 1 to 4 substituents selected from $R^d$, or R4 and R5 together with the atom to which they are attached form a 3- to 8-membered ring containing 0 to 2 heteroatoms selected from the group consisting of N, O and S, wherein said ring is unsubstituted or substituted with 1 to 3 substituents selected from $R^d$, or said ring is fused to aryl or heteroaryl, either of which is unsubstituted or substituted with 1 to 3 substituents selected from $R^d$;

A is
1) H,
2) ($C_1$-$C_6$)alkyl or
3) ($C_3$-$C_5$)cycloalkyl;
B is independently
1) H,
2) halogen or
3) ($C_1$-$C_6$)alkyl, or
symbols B together form a double or triple bond between the atoms to which they are attached;
R1 is
1) H,
2) ($C_1$-$C_6$)alkyl or
3) ($C_3$-$C_7$)cycloalkyl;
R2 is independently H, alkyl, alkenyl, alkynyl, cycloalkyl or a protecting group;
R3 is H, alkyl, cycloalkyl or a protecting group;
$R^a$ is independently
1) H,
2) halogen,
3) —$OR^b$,
4) ($C_1$-$C_6$)alkyl or
5) —$CF_3$;
$R^d$ is independently
1) a group selected from $R^c$,
2) ($C_1$-$C_6$)alkyl,
3) ($C_2$-$C_6$)alkenyl,
4) ($C_2$-$C_6$)alkynyl,
5) aryl,
6) aryl-($C_1$-$C_6$)alkyl,
7) heteroaryl-($C_1$-$C_6$)alkyl,
8) ($C_3$-$C_7$)cycloalkyl or
9) heterocyclyl, wherein alkyl, alkenyl, alkynyl, aryl and heteroaryl are unsubstituted or substituted with 1 to 4 substituents independently selected from $R^c$;
$R^b$ is independently
1) hydrogen,
2) ($C_1$-$C_6$)alkyl,
3) ($C_2$-$C_6$)alkenyl,
4) ($C_2$-$C_6$)alkynyl,
5) Cy or
6) Cy-($C_1$-$C_4$)alkyl;
$R^c$ is independently
1) a group selected from $R^a$,
2) —$NO_2$,
3) —$SR^b$,
4) —$NR^bR^b$,
5) —CN or
6) —$NR^bC(O)R^b$;

Cy is cycloalkyl, heterocyclyl, aryl or heteroaryl; and
n is the integer 1 or 2;
with a sulfonyl acid derivative of Formula IV

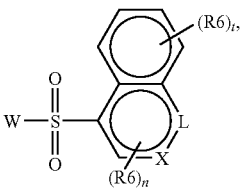

(IV)

wherein W is OH or a halogen;
R6 is independently
1) H,
2) halogen,
3) —$NO_2$,
4) —$NR^bR^b$,
5) —CN,
6) —$OR^b$,
7) —$SR^b$,
8) —$C(O)R^b$,
9) ($C_1$-$C_6$)alkyl,
10) ($C_2$-$C_6$)alkenyl,
11) ($C_2$-$C_6$)alkynyl,
12) ($C_3$-$C_7$)cycloalkyl or
13) —$CF_3$, wherein $R^b$ is defined as for Formula (III);
t is an integer from 0 to 3;
n is the integer 1 or 2;
X is a bond or C(R6); and
L is C(R6), S or N;
and wherein the compounds of Formulae III and IV are protected or unprotected.

10. A process for preparing a compound as claimed in claim 9, wherein the halogen of W is chlorine or bromine.

11. A pharmaceutical composition comprising a compound of Formula II as claimed in claim 1 as an active ingredient and a pharmaceutically acceptable diluent, carrier and/or excipient.

12. A method of imaging healthy or diseased tissues and/or organs possessing SSTR1 and/or SSTR4 receptors, comprising administering the compound of Formula II as defined in claim 1.

13. A method of imaging healthy or diseased tissues and/or organs as claimed in claim 12, wherein the tissues and/or organs are brain, blood vessels or tumors.

* * * * *